(12) United States Patent
Audonnet et al.

(10) Patent No.: US 6,348,196 B1
(45) Date of Patent: *Feb. 19, 2002

(54) FELINE POLYNUCLEOTIDE VACCINE FORMULA

(75) Inventors: Jean-Christophe Audonnet; Annabelle Bouchardon, both of Lyons; Philippe Baudu, Craponne; Michel Riviere, Ecully, all of (FR)

(73) Assignee: Merial, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/232,278

(22) Filed: Jan. 15, 1999

Related U.S. Application Data

(63) Continuation-in-part of application No. PCT/FR97/01315, filed on Jul. 15, 1997.

(30) Foreign Application Priority Data

Jul. 19, 1996 (FR) .............................. 96 09337

(51) Int. Cl.$^7$ ............................................ A61K 39/295
(52) U.S. Cl. ................ 424/202.1; 424/204.1; 424/221.1; 435/320.1; 514/44
(58) Field of Search .................... 435/320.1; 514/44; 424/202.1, 204.1, 207.1, 208.1, 221.1

(56) References Cited

U.S. PATENT DOCUMENTS 5,529,780 A * 6/1996 Paoletti et al. ............ 424/199.1
5,665,362 A * 9/1997 Inglis et al. .............. 424/205.1

FOREIGN PATENT DOCUMENTS

| AU | 74116/94 | * | 6/1995 |
| EP | 0 411 684 | * | 2/1991 |
| WO | WO 91/01332 | * | 2/1991 |
| WO | WO 94/06921 | * | 3/1994 |
| WO | WO 95/07987 | * | 3/1995 |
| WO | WO 95/20660 |   | 8/1995 |
| WO | WO 96/06934 |   | 3/1996 |
| WO | WO 96/18390 | * | 6/1996 |

OTHER PUBLICATIONS

Carlson et al., Journal of Virology, 55(3):574–582, Sep. 1985.*
Elder et al., Journal of Virology, 67(4):1869–76, Apr. 1993.*
Ertl et al., Annals New York Academy of Sciences, 772:77–87, 1996.*
Franke et al., Tierarztl. Prax. 18:629–632, 1990.*
Truyen et al., tierarztl Prax. 23:300–5, 1995.*
Herbert et al. ed., The Dictionary of Immunology, 4th ed., Academic Press, London, p. 163, 1995.*
Gonin et al., Vaccine Research, 4/4:217–227, 1995.*
Vennema et al., Virology 181:327–335, 1991.*
Andre et al., pp. 41–54 in Modern Vaccinology, ed. Kurstak e., Plenum Medical Book Comany, New York, 1994.*
R.C. Wardley et al, "The Use of Feline Herpesvirus and Baculovirus As Vaccine Vectors For the Gag and Env Genes of Feline Leukaemia Virus", J. General Virology, vol. 73, part 07 (1992) pp. 1811–1818.

* cited by examiner

Primary Examiner—Anthony C. Caputa
Assistant Examiner—Brenda G. Brumback
(74) Attorney, Agent, or Firm—Frommer Lawrence & Haug LLP; William S. Frommer; Thomas J. Kowalski

(57) ABSTRACT

Disclosed are plasmids that contain and express in vivo in a feline host cell nucleic acid molecules. The plasmid can include nucleic molecule(s) having sequence(s) encoding infectious peritonitis virus M; feline immunodeficiency virus env, or gag, or pro, or gag and pro, or env and gag and pro; rabies G; or feline leukemia virus env and/or gag. Compositions containing such plasmids, methods of use employing such plasmids, and kits involving such plasmids, are also disclosed.

16 Claims, 19 Drawing Sheets

```
   1 ATGGAAGGTCCAACGCACCCAAAACCCTCTAAAGATAAGACTTTCTCGTGGGACCTAATGATT
   1▶ MetGluGlyProThrHisProLysProSerLysAspLysThrPheSerTrpAspLeuMetIle

64 CTGGTGGGGTCTTACTAAGACTGGACGTGGGAATGGCCAATCCTAGTCCGCACCAAATATAT
  22▶ LeuValGlyValLeuLeuArgLeuAspValGlyMetAlaAsnProSerProHisGlnIleTyr

127 AATGTAACTTGGACAATAACCAACCTTGTAACTGGAACAAAGGCTAATGCCACCTCCATGTTG
  43▶ AsnValThrTrpThrIleThrAsnLeuValThrGlyThrLysAlaAsnAlaThrSerMetLeu

190 GGAACCCTGACAGACGCCTTCCCTACCATGTATTTTGACTTATGTGATATAATAGGAAATACA
  64▶ GlyThrLeuThrAspAlaPheProThrMetTyrPheAspLeuCysAspIleIleGlyAsnThr

253 TGGAACCCTTCAGATCAAGAACCATTCCCAGGGTATGGATGTGATCAGCCTATGAGGAGGTGG
  85▶ TrpAsnProSerAspGlnGluProPheProGlyTyrGlyCysAspGlnProMetArgArgTrp

316 CGACAGAGAAACACACCCTTTTATGTCTGTCCAGGACATGCCAACCGGAAGCAATGTGGGGGG
 106▶ ArgGlnArgAsnThrProPheTyrValCysProGlyHisAlaAsnArgLysGlnCysGlyGly

379 CCACAGGATGGGTTCTGCGCTGTATGGGGTTGCGAGACCACCGGGGAAACCTATTGGAGACCC
 127▶ ProGlnAspGlyPheCysAlaValTrpGlyCysGluThrThrGlyGluThrTyrTrpArgPro

442 ACCTCCTCATGGGACTACATCACAGTAAAAAAAGGGGTTACTCAGGGAATATATCAATGTAGT
 148▶ ThrSerSerTrpAspTyrIleThrValLysLysGlyValThrGlnGlyIleTyrGlnCysSer

505 GGAGGTGGTTGGTGTGGGCCTGTTACGATAAAGCTGTTCACTCCTCGACAACGGGAGCTAGT
 169▶ GlyGlyGlyTrpCysGlyProCysTyrAspLysAlaValHisSerSerThrThrGlyAlaSer

568 GAAGGGGGCCGGTGCAACCCCTTGATCTTGCAATTTACCCAAAAGGGAAGACAAACATCTTGG
 190▶ GluGlyGlyArgCysAsnProLeuIleLeuGlnPheThrGlnLysGlyArgGlnThrSerTrp

631 GATGGACCTAAGTCATGGGGGCTACGACTATACCGTTCAGGATATGACCCTATAGCCCTGTTC
 211▶ AspGlyProLysSerTrpGlyLeuArgLeuTyrArgSerGlyTyrAspProIleAlaLeuPhe

694 TCGGTATCCCGGCAAGTAATGACCATTACGCCGCCTCAGGCCATGGGACCAAATCTAGTCCTG
 232▶ SerValSerArgGlnValMetThrIleThrProProGlnAlaMetGlyProAsnLeuValLeu

757 CCTGATCAAAAACCCCCATCCAGGCAATCTCAAATAGAGTCCCGAGTAACACCTCACCATTCC
 253▶ ProAspGlnLysProProSerArgGlnSerGlnIleGluSerArgValThrProHisHisSer

820 CAAGGCAACGGAGGCACCCCAGGTGTAACTCTTGTTAATGCCTCCATTGCCCCTCTACGTACC
 274▶ GlnGlyAsnGlyGlyThrProGlyValThrLeuValAsnAlaSerIleAlaProLeuArgThr

883 CCTGTCACCCCCGCAAGTCCCAAACGTATAGGGACCGGAAATAGGTTAATAAATTTAGTGCAA
 295▶ ProValThrProAlaSerProLysArgIleGlyThrGlyAsnArgLeuIleAsnLeuValGln

946 GGGACATACCTAGCCTTAAATGCCACCGACCCCAACAAAACTAAAGACTGTTGGCTCTGCCTG
 316▶ GlyThrTyrLeuAlaLeuAsnAlaThrAspProAsnLysThrLysAspCysTrpLeuCysLeu

1009 GTTTCTCGACCACCTTATTACGAAGGGATTGCAATCTTAGGTAACTACAGCAACCAAACAAAC
 337▶ ValSerArgProProTyrTyrGluGlyIleAlaIleLeuGlyAsnTyrSerAsnGlnThrAsn

1072 CCCTCCCCATCCTGCCTATCTACTCCGCAACATAAGCTAACTATATCTGAGGTGTCAGGGCAA
 358▶ ProSerProSerCysLeuSerThrProGlnHisLysLeuThrIleSerGluValSerGlyGln

1135 GGACTGTGCATAGGGACTGTTCCTAAGACCCACCAGGCTTTGTGCAATAAGACACAACAGGGA
 379▶ GlyLeuCysIleGlyThrValProLysThrHisGlnAlaLeuCysAsnLysThrGlnGlnGly

1198 CATACAGGGGCTCACTATCTAGCCGCCCCAATGGCACCTATTGGGCCTGTAACACTGGACTC
 400▶ HisThrGlyAlaHisTyrLeuAlaAlaProAsnGlyThrTyrTrpAlaCysAsnThrGlyLeu
```

1261 ACCCCATGCATTTCCATGGCAGTGCTCAATTGGACCTCTGATTTTTGTGTCTTAATCGAATTA
 421▶ ThrProCysIleSerMetAlaValLeuAsnTrpThrSerAspPheCysValLeuIleGluLeu

1324 TGGCCCAGAGTGACCTACCATCAACCCGAATACATTTACACACATTTCGACAAAGCTGTCAGG
 442▶ TrpProArgValThrTyrHisGlnProGluTyrIleTyrThrHisPheAspLysAlaValArg

1387 TTCCGAAGAGAACCAATATCACTAACCGTTGCCCTTATAATGGGAGGACTCACTGTAGGGGC
 463▶ PheArgArgGluProIleSerLeuThrValAlaLeuIleMetGlyGlyLeuThrValGlyGly

1450 ATAGCCGCGGGGGTCGGAACAGGGACTAAAGCCCTCCTTGAAACAGCCCAGTTCAGACAACTA
 484▶ IleAlaAlaGlyValGlyThrGlyThrLysAlaLeuLeuGluThrAlaGlnPheArgGlnLeu

1513 CAAATGGCTATGCACGCAGACATCCAGGCCCTAGAAGAGTCAATTAGTGCCTTAGAAAAATCC
 505▶ GlnMetAlaMetHisAlaAspIleGlnAlaLeuGluGluSerIleSerAlaLeuGluLysSer

1576 CTGACCTCCCTCTCCGAGGTAGTCTTACAAAATAGACGGGGCCTAGATATTCTGTTCTTACAA
 526▶ LeuThrSerLeuSerGluValValLeuGlnAsnArgArgGlyLeuAspIleLeuPheLeuGln

1639 AAGGGAGGGCTCTGTGCCGCCTTAAAGGAAGAATGCTGCTTCTATGCAGATCACACCGGACTC
 547▶ LysGlyGlyLeuCysAlaAlaLeuLysGluGluCysCysPheTyrAlaAspHisThrGlyLeu

1702 GTCAGAGACAATATGGCTAAATTAAGAGAAAGACTGAAACAGCGACAACAACTGTTTGACTCC
 568▶ ValArgAspAsnMetAlaLysLeuArgGluArgLeuLysGlnArgGlnGlnLeuPheAspSer

1765 CAACAGGGATGGTTTGAAGGATGGTTCAACAAGTCCCCCTGGTTTACAACCCTAATTTCCTCC
 589▶ GlnGlnGlyTrpPheGluGlyTrpPheAsnLysSerProTrpPheThrThrLeuIleSerSer

1828 ATTATAGGCCCCTTACTAATCCTACTCCTAATTCTCCTCTTCGGCCCATGCATCCTTAACCGA
 610▶ IleIleGlyProLeuLeuIleLeuLeuLeuIleLeuLeuPheGlyProCysIleLeuAsnArg

1891 TTAGTGCAATTCGTAAAAGACAGAATATCTGTGGTACAAGCCTTAATTTTAACCCAACAGTAC
 631▶ LeuValGlnPheValLysAspArgIleSerValValGlnAlaLeuIleLeuThrGlnGlnTyr

1954 CAACAGATACAGCAATATGATCCGGACCGACCATGA
 652▶ GlnGlnIleGlnGlnTyrAspProAspArgPro***

```
   1 ATGTCTGGAGCCTCTAGTGGGACAGCCATTGGGGCTCATCTGTTTGGGGTCTCACCTGAATAC
   1►MetSerGlyAlaSerSerGlyThrAlaIleGlyAlaHisLeuPheGlyValSerProGluTyr

64 AGGGTGTTGATCGGAGACGAGGGAGCCGGACCCTCAAGGTCTCTTTCTGAGGTTTCATTTTCG
  22►ArgValLeuIleGlyAspGluGlyAlaGlyProSerArgSerLeuSerGluValSerPheSer

127 GTTTGGTACCAAAGACGCGCGGCACGTCTTGTCATTTTTTGTCTGGTTGCGTCTTTTCTTGTC
  43►ValTrpTyrGlnArgArgAlaAlaArgLeuValIlePheCysLeuValAlaSerPheLeuVal

190 CCTTGTCTAACCTTTTTAATTGCAGAAACCGTCATGGGCCAAACTATAACTACCCCCTTAAGC
  64►ProCysLeuThrPheLeuIleAlaGluThrValMetGlyGlnThrIleThrThrProLeuSer

253 CTCACCCTTGATCACTGGTCTGAAGTCCGGGCACGAGCCCATAATCAAGGTGTCGAGGTCCGG
  85►LeuThrLeuAspHisTrpSerGluValArgAlaArgAlaHisAsnGlnGlyValGluValArg

316 AAAAAGAAATGGATTACCTTATGTGAGGCCGAATGGGTGATGATGAATGTGGGCTGGCCCCGA
 106►LysLysLysTrpIleThrLeuCysGluAlaGluTrpValMetMetAsnValGlyTrpProArg

379 GAAGGAACTTTTTCTCTTGATAGCATTTCCCAGGTTGAAAAGAAGATCTTCGCCCCGGGACCA
 127►GluGlyThrPheSerLeuAspSerIleSerGlnValGluLysLysIlePheAlaProGlyPro

442 TATGGACACCCCGACCAAGTTCCTTACATTACTACATGGAGATCCTTAGCCACAGACCCCCCT
 148►TyrGlyHisProAspGlnValProTyrIleThrThrTrpArgSerLeuAlaThrAspProPro

505 TCGTGGGTTCGTCCGTTCCTACCCCCTCCCAAACCTCCCACACCCCTCCCTCAACCTCTTTCG
 169►SerTrpValArgProPheLeuProProProLysProProThrProLeuProGlnProLeuSer

568 CCGCAGCCCTCCGCCCTCTTACCTCTTCCCTCTACCCCGTTCTCCCCAAGCCAGACCCCCCC
 190►ProGlnProSerAlaProLeuThrSerSerLeuTyrProValLeuProLysProAspProPro

631 AAACCGCCTGTGTTACCGCCTGATCCTTCTTCCCCTTTAATTGATCTCTTAACAGAAGAGCCA
 211►LysProProValLeuProProAspProSerSerProLeuIleAspLeuLeuThrGluGluPro

694 CCTCCCTATCCGGGGGGTCACGGGCCACCGCCATCAGGTCCTAGGACCCCAACCGCTTCCCCG
 232►ProProTyrProGlyGlyHisGlyProProProSerGlyProArgThrProThrAlaSerPro

757 ATTGCAAGCCGGCTAAGGGAACGACGAGAAAACCCTGCTGAAGAATCGCAAGCCCTCCCCTTG
 253►IleAlaSerArgLeuArgGluArgArgGluAsnProAlaGluGluSerGlnAlaLeuProLeu

820 AGGGAAGGCCCCAACAACCGACCCCAGTATTGGCCATTCTCAGCTTCAGACTTGTATAACTGG
 274►ArgGluGlyProAsnAsnArgProGlnTyrTrpProPheSerAlaSerAspLeuTyrAsnTrp

883 AAGTCGCATAACCCCCCTTTCTCCCAAGATCCAGTGGCCCTAACTAACCTAATTGAGTCCATT
 295►LysSerHisAsnProProPheSerGlnAspProValAlaLeuThrAsnLeuIleGluSerIle

946 TTAGTGACGCATCAACCAACCTGGGACGACTGCCAGCAGCTCTTGCAGGCACTCCTGACAGGC
 316►LeuValThrHisGlnProThrTrpAspAspCysGlnGlnLeuLeuGlnAlaLeuLeuThrGly

1009 GAAGAAAGGCAAAGGGTCCTTCTTGAGGCCCGAAAGCAGGTTCCAGGCGAGGACGGACGGCCA
 337►GluGluArgGlnArgValLeuLeuGluAlaArgLysGlnValProGlyGluAspGlyArgPro

1072 ACCCAACTACCCAATGTCATTGACGAGACTTTCCCCTTGACCCGTCCCAACTGGGATTTTGCT
 358►ThrGlnLeuProAsnValIleAspGluThrPheProLeuThrArgProAsnTrpAspPheAla

1135 ACGCCGGCAGGTAGGGAGCACCTACGCCTTTATCGCCAGTTGCTATTAGCGGGTCTCCGCGGG
 379►ThrProAlaGlyArgGluHisLeuArgLeuTyrArgGlnLeuLeuLeuAlaGlyLeuArgGly
```

FIG. 5A

| FIG. 5 | FIG. 5A |
|---|---|
| | FIG. 5B |
| | FIG. 5C |

```
1198 GCTGCAAGACGCCCCACTAATTTGGCACAGGTAAAGCAGGTTGTACAAGGGAAAGAGGAAACC
 400▶AlaAlaArgArgProThrAsnLeuAlaGlnValLysGlnValValGlnGlyLysGluGluThr

1261 CCAGCAGCATTTTTAGAAAGATTAAAAGAGGCTTATAGAATGTACACTCCCTATGACCCTGAG
 421▶ProAlaAlaPheLeuGluArgLeuLysGluAlaTyrArgMetTyrThrProTyrAspProGlu

1324 GACCCAGGGCAAGCGGCTAGTGTTATCCTATCCTTTATATACCAGTCTAGCCCAGATATAAGA
 442▶AspProGlyGlnAlaAlaSerValIleLeuSerPheIleTyrGlnSerSerProAspIleArg

1387 AATAAGTTACAAAGGCTAGAAGGCCTACAAGGGTTCACCCTATCTGATCTGCTAAAAGAGGCA
 463▶AsnLysLeuGlnArgLeuGluGlyLeuGlnGlyPheThrLeuSerAspLeuLeuLysGluAla

1450 GAAAAGATATACAACAAAAGGGAGACCCCAGAGGAAAGGGAAGAAAGATTATGGCAGCGACAG
 484▶GluLysIleTyrAsnLysArgGluThrProGluGluArgGluGluArgLeuTrpGlnArgGln

1513 GAAGAAAGAGATAAAAAGCGCCACAAGGAGATGACTAAAGTTCTGGCCACAGTAGTTGCTCAG
 505▶GluGluArgAspLysLysArgHisLysGluMetThrLysValLeuAlaThrValValAlaGln

1576 AATAGAGATAAGGATAGAGAAGAAAGTAAACTGGGGGATCAAAGGAAAATACCTCTGGGGAAA
 526▶AsnArgAspLysAspArgGluGluSerLysLeuGlyAspGlnArgLysIleProLeuGlyLys

1639 GACCAGTGTGCCTATTGCAAGGAAAAGGGGCATTGGGTTCGCGATTGCCCCAAACGACCCAGG
 547▶AspGlnCysAlaTyrCysLysGluLysGlyHisTrpValArgAspCysProLysArgProArg

1702 AAGAAACCCGCCAACTCCACTCTCCTCAACTTAGGAGATTAGGAGAGTCAGGGCCAGGACCCC
 568▶LysLysProAlaAsnSerThrLeuLeuAsnLeuGlyAsp•••
                                       1▶GluIleArgArgValArgAlaArgThrPr

1765 CCCCCCTGAGCCCAGGATAACCTTAAAAATAGGGGGGCAACCGGTGACTTTTCTGGTGGACAC
  10▶oProProGluProArgIleThrLeuLysIleGlyGlyGlnProValThrPheLeuValAspTh

1828 GGGAGCCCAGCACTCAGTACTGACTCGACCAGATGGACCTCTCAGTGACCGCACAGCCCTGGT
  31▶rGlyAlaGlnHisSerValLeuThrArgProAspGlyProLeuSerAspArgThrAlaLeuVa

1891 GCAAGGAGCCACGGGAAGCAAAAACTACCGGTGGACCACCGACAGGAGGGTACAACTGGCAAC
  52▶lGlnGlyAlaThrGlySerLysAsnTyrArgTrpThrThrAspArgArgValGlnLeuAlaTh

1954 CGGTAAGGTGACTCATTCTTTTTTATATGTACCTGAATGTCCCTACCCGTTATTAGGGAGAGA
  73▶rGlyLysValThrHisSerPheLeuTyrValProGluCysProTyrProLeuLeuGlyArgAs

2017 CCTATTAACTAAACTTAAGGCCCAAATCCATTTTACCGGAGAAGGGGCTAATGTTGTTGGGCC
  94▶pLeuLeuThrLysLeuLysAlaGlnIleHisPheThrGlyGluGlyAlaAsnValValGlyPr

2080 CAGGGGTTTACCCCTACAAGTCCTTACTTTACAATTAGAAGAGGAGTATCGGCTATTTGAGCC
 115▶oArgGlyLeuProLeuGlnValLeuThrLeuGlnLeuGluGluGluTyrArgLeuPheGluPr

2143 AGAAAGTACACAAAAACAGGAGATGGACACTTGGCTTAAAAACTTTCCCCAGGCGTGGGCAGA
 136▶oGluSerThrGlnLysGlnGluMetAspThrTrpLeuLysAsnPheProGlnAlaTrpAlaGl
```

| | FIG. 5A |
|---|---|
| FIG. 5 | FIG. 5B |
| | FIG. 5C |

FIG. 5B

```
2206 AACAGGAGGTATGGGAATGGCTCATTGTCAAGCCCCGTTCTCATTCAACTTAAGGCTACTGC
157▶ uThrGlyGlyMetGlyMetAlaHisCysGlnAlaProValLeuIleGlnLeuLysAlaThrAl

2269 CACTCCAATCTCCATCCGACAGTATCCTATGCCCCATGAAGCGTACCAGGGAATTAAGCCTCA
178▶ aThrProIleSerIleArgGlnTyrProMetProHisGluAlaTyrGlnGlyIleLysProHi

2332 TATAAGAAGAATGCTAGATCAAGGCATCCTCAAGCCCTGCCAGTCCCCATGGAATACACCCTT
199▶ sIleArgArgMetLeuAspGlnGlyIleLeuLysProCysGlnSerProTrpAsnThrProLe

2395 ATTACCTGTTAAGAAGCCAGGGACCGAGGATTACAGACCAGTGCAGGACTTAAGAGAAGTAAA
220▶ uLeuProValLysLysProGlyThrGluAspTyrArgProValGlnAspLeuArgGluValAs

2458 CAAAAGAGTAGAAGACATCCATCCTACTGTGCCAAATCCATATAACCTCCTTAGCACCCTCCC
241▶ nLysArgValGluAspIleHisProThrValProAsnProTyrAsnLeuLeuSerThrLeuPr

2521 GCCGTCTCACCCTTGGTACACTGTCCTAGATTTAAAGGACGCTTTTTTCTGCCTGCGACTACA
262▶ oProSerHisProTrpTyrThrValLeuAspLeuLysAspAlaPhePheCysLeuArgLeuHi

2584 CTCTGAGAGTCAGTTACTTTTTGCATTTGAATGGAGAGATCCAGAAATAGGACTGTCAGGGCA
283▶ sSerGluSerGlnLeuLeuPheAlaPheGluTrpArgAspProGluIleGlyLeuSerGlyGl

2647 ACTAACCTGGACACGCCTTCCTCAGGGGTTCAAGAATAGCCCCACCCTATTTGATGAGGCCCT
304▶ nLeuThrTrpThrArgLeuProGlnGlyPheLysAsnSerProThrLeuPheAspGluAlaLe

2710 GCACTCAGACCTGGCCGATTTCAGGGTAAGGTACCCGGCTCTAGTCCTCCTACAATATGTAGA
325▶ uHisSerAspLeuAlaAspPheArgValArgTyrProAlaLeuValLeuLeuGlnTyrValAs

2773 TGACCTCTTGCTGGCTGCGGCAACCAGGACTGAATGCCTGGAAGGGACTAAGGCACTCCTTGA
346▶ pAspLeuLeuLeuAlaAlaAlaThrArgThrGluCysLeuGluGlyThrLysAlaLeuLeuGl

2836 GACTTTGGGCAATAAGGGGTACCGAGCCTCTGGAAAGAAGGCCCAAATTTGCCTGCAAGAAGT
367▶ uThrLeuGlyAsnLysGlyTyrArgAlaSerGlyLysLysAlaGlnIleCysLeuGlnGluVa

2899 CACATACCTGGGGTACTCTTTAAAAGATGGCCAAAGGTGGCTTACCAAAGCTCGGAAAGAAGC
388▶ lThrTyrLeuGlyTyrSerLeuLysAspGlyGlnArgTrpLeuThrLysAlaArgLysGluAl

2962 CATCCTATCCATCCCTGTGCCTAAAAACCCACGACAAGTGAGAGAGTTCCTTGGAACTGCAG
409▶ aIleLeuSerIleProValProLysAsnProArgGlnValArgGluPheLeuGlyThrAla
```

FIG. 5C

| FIG. 5 | FIG. 5A |
| --- | --- |
| | FIG. 5B |
| | FIG. 5C |

SEQUENCE LISTING

```
<160> NUMBER OF SEQ ID NOS: 30

<210> SEQ ID NO 1
<211> LENGTH: 29
<212> TYPE: DNA
<213> ORGANISM: Feline leukemia virus

<400> SEQUENCE: 1
tttgtcgacc atggaaagtc caacgcacc                              29

<210> SEQ ID NO 2
<211> LENGTH: 28
<212> TYPE: DNA
<213> ORGANISM: Feline leukemia virus

<400> SEQUENCE: 2
tttggatcct catggtcggt ccggatcg                               28

<210> SEQ ID NO 3
<211> LENGTH: 29
<212> TYPE: DNA
<213> ORGANISM: Feline leukemia virus

<400> SEQUENCE: 3
tttgtcgaca tggaaggtcc aacgcaccc                              29

<210> SEQ ID NO 4
<211> LENGTH: 32
<212> TYPE: DNA
<213> ORGANISM: Feline leukemia virus

<400> SEQUENCE: 4
ttggatcctc atggtcggtc cggatcatat tg                          32

<210> SEQ ID NO 5
<211> LENGTH: 1989
<212> TYPE: DNA
<213> ORGANISM: Feline leukemia virus

<400> SEQUENCE: 5
atggaaggtc caacgcaccc aaaaccctct aaagataaga ctttctcgtg ggacctaatg      60
attctggtgg gggtcttact aagactggac gtgggaatgg ccaatcctag tccgcaccaa     120
atatataatg taacttggac aataaccaac cttgtaactg gaacaaaggc taatgccacc     180
tccatgttgg gaaccctgac agacgccttc cctaccatgt attttgactt atgtgatata     240
ataggaaata catggaaccc ttcagatcaa gaaccattcc cagggtatgg atgtgatcag     300
cctatgagga ggtggcgaca gagaaacaca cccttttatg tctgtccagg acatgccaac     360
cggaagcaat gtgggggcc acaggatggg ttctgcgctg tatggggttg cgagaccacc     420
ggggaaacct attggagacc cacctcctca tgggactaca tcacagtaaa aaaagggggtt     480 actcagggaa tatatcaatg tagtggaggt ggttggtgtg ggccctgtta cgataaagct     540
gttcactcct cgacaacggg agctagtgaa gggggccggt gcaaccccctt gatcttgcaa     600
```

```
tttacccaaa agggaagaca aacatcttgg gatggaccta agtcatgggg gctacgacta      660
taccgttcag gatatgaccc tatagccctg ttctcggtat cccggcaagt aatgaccatt      720
acgccgcctc aggccatggg accaaatcta gtcctgcctg atcaaaaacc cccatccagg      780
caatctcaaa tagagtcccg agtaacacct caccattccc aaggcaacgg aggcacccca      840
ggtgtaactc ttgttaatgc ctccattgcc cctctacgta cccctgtcac ccccgcaagt      900
cccaaacgta tagggaccgg aaataggtta ataaatttag tgcaagggac atacctagcc      960
ttaaatgcca ccgaccccaa caaaactaaa gactgttggc tctgcctggt ttctcgacca     1020
ccttattacg aagggattgc aatcttaggt aactacagca accaaacaaa cccctcccca     1080
tcctgcctat ctactccgca acataagcta actatatctg aggtgtcagg caaggactg      1140 tgcataggga ctgttcctaa gacccaccag gctttgtgca ataagacaca acagggacat     1200 acagggctc actatctagc cgcccccaat ggcacctatt gggcctgtaa cactggactc      1260
accccatgca tttccatggc agtgctcaat tggacctctg attttgtgt cttaatcgaa       1320 ttatggccca gagtgaccta ccatcaaccc gaatacattt acacacattt cgacaaagct      1380
gtcaggttcc gaagagaacc aatatcacta accgttgccc ttataatggg aggactcact      1440
gtaggggcga tagccgcggg ggtcggaaca gggactaaag ccctccttga aacagcccag     1500
ttcagacaac tacaaatggc tatgcacgca gacatccagg ccctagaaga gtcaattagt     1560
gccttagaaa aatccctgac ctccctctcc gaggtagtct acaaaatag acggggccta      1620 gatattctgt tcttacaaaa gggagggctc tgtgccgcct taaaggaaga atgctgcttc     1680
tatgcagatc acaccggact cgtcagagac aatatggcta aattaagaga aagactgaaa     1740
cagcgacaac aactgtttga ctcccaacag ggatggtttg aaggatggtt caacaagtcc     1800
ccctggttta caaccctaat ttcctccatt ataggcccct tactaatcct actcctaatt     1860
ctcctcttcg gccatgcat ccttaaccga ttagtgcaat tcgtaaaaga cagaatatct     1920
gtggtacaag ccttaatttt aacccaacag taccaacaga tacagcaata tgatccggac     1980
cgaccatga                                                                1989

<210> SEQ ID NO 6
<211> LENGTH: 33
<212> TYPE: DNA
<213> ORGANISM: Feline leukemia virus

<400> SEQUENCE: 6
ttgtcgacat gtctggagcc tctagtggga cag                                     33

<210> SEQ ID NO 7
<211> LENGTH: 40
<212> TYPE: DNA
<213> ORGANISM: Feline leukemia virus

<400> SEQUENCE: 7
ttggatcctt atttaattac tgcagttcca aggaactctc                               40

<210> SEQ ID NO 8
<211> LENGTH: 3022
<212> TYPE: DNA
<213> ORGANISM: Feline leukemia virus

<400> SEQUENCE: 8
atgtctggag cctctagtgg gacagccatt ggggctcatc tgtttgggt ctcacctgaa          60 tacagggtgt tgatcggaga cgagggagcc ggaccctcaa ggtctctttc tgaggtttca        120
```

-continued

| | |
|---|---|
| ttttcggttt ggtaccaaag acgcgcggca cgtcttgtca ttttttgtct ggttgcgtct | 180 |
| tttcttgtcc cttgtctaac ctttttaatt gcagaaaccg tcatgggcca aactataact | 240 |
| accccttaa gcctcaccct tgatcactgg tctgaagtcc gggcacgagc cataatcaa | 300 |
| ggtgtcgagg tccggaaaaa gaaatggatt accttatgtg aggccgaatg ggtgatgatg | 360 |
| aatgtgggct ggccccgaga aggaactttt tctcttgata gcatttccca ggttgaaaag | 420 |
| aagatcttcg ccccgggacc atatggacac cccgaccaag ttccttacat tactacatgg | 480 |
| agatccttag ccacagaccc ccttcgtgg gttcgtccgt tcctaccccc tcccaaacct | 540 |
| cccacacccc tccctcaacc tctttcgccg cagccctccg cccctcttac ctcttccctc | 600 |
| tacccgttc tccccaagcc agacccccc aaaccgcctg tgttaccgcc tgatccttct | 660 |
| tcccctttaa ttgatctctt aacagaagag ccacctccct atccgggggg tcacgggcca | 720 |
| ccgccatcag gtcctaggac cccaaccgct tccccgattg caagccggct aagggaacga | 780 |
| cgagaaaacc ctgctgaaga tcgcaagcc ctcccttga gggaaggccc caacaaccga | 840 |
| ccccagtatt ggccattctc agcttcgac ttgtataact ggaagtcgca taacccccct | 900 |
| ttctcccaag atccagtggc cctaactaac ctaattgagt ccattttagt gacgcatcaa | 960 |
| ccaacctggg acgactgcca gcagctcttg caggcactcc tgacaggcga agaaaggcaa | 1020 |
| aggtgtccttc ttgaggcccg aaagcaggtt ccaggcgagg acggacggcc aacccaacta | 1080 |
| cccaatgtca ttgacgagac tttccccttg accgtccca actgggattt tgctacgccg | 1140 |
| gcaggtaggg agcacctacg cctttatcgc cagttgctat tagcgggtct ccgcggggct | 1200 |
| gcaagacgcc ccactaattt ggcacaggta agcaggttg tacaagggaa agaggaaacg | 1260 |
| ccagcagcat ttttagaaag attaaaagag gcttatagaa tgtacactcc ctatgaccct | 1320 |
| gaggacccag ggcaagcggc tagtgttatc ctatcctta tataccagtc tagcccagat | 1380 |
| ataagaaata agttacaaag gctagaaggc ctacaagggt tcaccctatc tgatctgcta | 1440 |
| aaagaggcag aaaagatata caacaaaagg gagacccag aggaaaggga agaaagatta | 1500 |
| tggcagcgac aggaagaaag agataaaaag cgccacaagg agatgactaa agttctggcc | 1560 |
| acagtagttg ctcagaatag agataaggat agagaagaaa gtaaactggg ggatcaaagg | 1620 |
| aaaataccct ggggaaaga ccagtgtgcc tattgcaagg aaaagggggca ttgggttcgc | 1680 |
| gattgcccca acgacccag gaagaaaccc gccaactcca ctctcctcaa cttaggagat | 1740 |
| aggagagtca gggccaggac cccccccct gagcccagga taaccttaaa aataggggg | 1800 |
| caaccggtga ctttctggt ggacacggga gcccagcact cagtactgac tcgaccagat | 1860 |
| ggacctctca gtgaccgcac agccctggtg caaggagcca cggaagcaa aaactaccgg | 1920 |
| tggaccaccg acaggagggt acaactggca accggtaagg tgactcattc tttttatat | 1980 |
| gtacctgaat gtccctaccc gttattaggg agagacctat taactaaact taaggcccaa | 2040 |
| atccattta ccggagaagg ggctaatgtt gttgggccca ggggtttacc cctacaagtc | 2100 |
| cttactttac aattagaaga ggagtatcgg ctatttgagc cagaaagtac acaaaaacag | 2160 |
| gagatggaca cttggcttaa aaactttccc caggcgtggg cagaaacagg aggtatggga | 2220 |
| atggctcatt gtcaagcccc cgttctcatt caacttaagg ctactgccac tccaatctcc | 2280 |
| atccgacagt atcctatgcc ccatgaagcg taccaggaa ttaagcctca tataagaaga | 2340 |
| atgctagatc aaggcatcct caagccctgc cagtccccat ggaatacacc cttattcct | 2400 |
| gttaagaagc cagggaccga ggattacaga ccagtgcagg acttaagaga agtaaacaaa | 2460 |
| agagtagaag acatccatcc tactgtgcca aatccatata acctccttag caccctcccg | 2520 |

-continued

```
ccgtctcacc cttggtacac tgtcctagat ttaaaggacg cttttttctg cctgcgacta    2580
cactctgaga gtcagttact ttttgcattt gaatggagag atccagaaat aggactgtca    2640
gggcaactaa cctggacacg ccttcctcag gggttcaaga atagcccac cctatttgat     2700 gaggccctgc actcagacct ggccgatttc agggtaaggt acccggctct agtcctccta    2760
caatatgtag atgacctctt gctggctgcg gcaaccagga ctgaatgcct ggaagggact    2820
aaggcactcc ttgagacttt gggcaataag gggtaccgag cctctggaaa gaaggcccaa    2880
atttgcctgc aagaagtcac atacctgggg tactctttaa aagatggcca aaggtggctt    2940
accaaagctc ggaaagaagc catcctatcc atccctgtgc ctaaaaaccc acgacaagtg    3000
agagagttcc ttggaactgc ag                                             3022
```

<210> SEQ ID NO 9
<211> LENGTH: 34
<212> TYPE: DNA
<213> ORGANISM: Feline Panleukopaenia Virus

<400> SEQUENCE: 9

```
tgctctagag caatgagtga tggagcagtt caac                                34
```

<210> SEQ ID NO 10
<211> LENGTH: 33
<212> TYPE: DNA
<213> ORGANISM: Feline Panleukopaenia Virus

<400> SEQUENCE: 10

```
cgcggatcca ttaatataat tttctaggtg cta                                 33
```

<210> SEQ ID NO 11
<211> LENGTH: 38
<212> TYPE: DNA
<213> ORGANISM: Feline infectious peritonitis virus

<400> SEQUENCE: 11

```
ataagaatgc ggccgcatga ttgtgctcgt aacttgcc                            38
```

<210> SEQ ID NO 12
<211> LENGTH: 25
<212> TYPE: DNA
<213> ORGANISM: Feline infectious peritonitis virus

<400> SEQUENCE: 12

```
cgtacatgtg gaattccact ggttg                                          25
```

<210> SEQ ID NO 13
<211> LENGTH: 25
<212> TYPE: DNA
<213> ORGANISM: Feline infectious peritonitis virus

<400> SEQUENCE: 13

```
agagttgcaa ctagttctga ttttg                                          25
```

<210> SEQ ID NO 14
<211> LENGTH: 37
<212> TYPE: DNA
<213> ORGANISM: Feline infectious peritonitis virus

<400> SEQUENCE: 14

```
ataagaatgc ggccgcttag tggacatgca cttttc                              37
```

-continued

```
<210> SEQ ID NO 15
<211> LENGTH: 37
<212> TYPE: DNA
<213> ORGANISM: Feline infectious peritonitis virus

<400> SEQUENCE: 15
acgcgtcgac ccaccatgaa gtacattttg ctaatac                    37

<210> SEQ ID NO 16
<211> LENGTH: 36
<212> TYPE: DNA
<213> ORGANISM: Feline infectious peritonitis virus

<400> SEQUENCE: 16
cgcggatcct tacaccatat gtaataattt ttcatg                     36

<210> SEQ ID NO 17
<211> LENGTH: 35
<212> TYPE: DNA
<213> ORGANISM: Feline infectious peritonitis virus

<400> SEQUENCE: 17
acgcgtcgac gccatggcca cagggaca acgcg                        35

<210> SEQ ID NO 18
<211> LENGTH: 36
<212> TYPE: DNA
<213> ORGANISM: Feline infectious peritonitis virus

<400> SEQUENCE: 18
cgcggatcct tagttcgtaa cctcatcaat catctc                     36

<210> SEQ ID NO 19
<211> LENGTH: 36
<212> TYPE: DNA
<213> ORGANISM: Feline herpesvirus 1

<400> SEQUENCE: 19
aaaactgcag aatcatgtcc actcgtggcg atcttg                     36

<210> SEQ ID NO 20
<211> LENGTH: 40
<212> TYPE: DNA
<213> ORGANISM: Feline herpesvirus 1

<400> SEQUENCE: 20
ataagaatgc ggccgcttag acaagatttg tttcagtatc                 40

<210> SEQ ID NO 21
<211> LENGTH: 36
<212> TYPE: DNA
<213> ORGANISM: Feline herpesvirus 1

<400> SEQUENCE: 21
aaaactgcag ccaatgatga cacgtctaca tttttg                     36

<210> SEQ ID NO 22
<211> LENGTH: 33
<212> TYPE: DNA
<213> ORGANISM: Feline herpesvirus 1

<400> SEQUENCE: 22
ggaagatctt taaggatggt gagttgtatg tat                        33
```

```
<210> SEQ ID NO 23
<211> LENGTH: 33
<212> TYPE: DNA
<213> ORGANISM: Feline calicivirus

<400> SEQUENCE: 23
acgcgtcgac gcatgtgctc aacctgcgct aac                    33

<210> SEQ ID NO 24
<211> LENGTH: 31
<212> TYPE: DNA
<213> ORGANISM: Feline calicivirus

<400> SEQUENCE: 24
cgcggatcct cataacttag tcatgggact c                      31

<210> SEQ ID NO 25
<211> LENGTH: 36
<212> TYPE: DNA
<213> ORGANISM: Feline immunodeficiency virus

<400> SEQUENCE: 25
aaaactgcag aaggaatggc agaaggattt gcagcc                 36

<210> SEQ ID NO 26
<211> LENGTH: 36
<212> TYPE: DNA
<213> ORGANISM: Feline immunodeficiency virus

<400> SEQUENCE: 26
cgcggatcct cattcctcct ctttttcaga catgcc                 36

<210> SEQ ID NO 27
<211> LENGTH: 32
<212> TYPE: DNA
<213> ORGANISM: Feline immunodeficiency virus

<400> SEQUENCE: 27
acgcgtcgac atggggaatg gacaggggcg ag                     32

<210> SEQ ID NO 28
<211> LENGTH: 33
<212> TYPE: DNA
<213> ORGANISM: Feline immunodeficiency virus

<400> SEQUENCE: 28
tgaagatctt cactcatccc cttcaggaag agc                    33

<210> SEQ ID NO 29
<211> LENGTH: 33
<212> TYPE: DNA
<213> ORGANISM: Rabies virus

<400> SEQUENCE: 29
aaaactgcag agatggttcc tcaggctctc ctg                    33

<210> SEQ ID NO 30
<211> LENGTH: 34
<212> TYPE: DNA
<213> ORGANISM: Rabies virus

<400> SEQUENCE: 30
cgcggatcct cacagtctgg tctcaccccc actc                   34
```

FELINE POLYNUCLEOTIDE VACCINE FORMULA

This is a continuation-in-part of copending International Application PCT/FR97/01315 having an international filing date of July 15, 1997, and designating the U.S. and claiming priority from French Application No. 96/09337, filed July 19, 1996. Reference is also made to the concurrently filed applications of Audonnet et al., Ser. Nos. 09/232,468, 09/232,477, 09/232,279, 09/232,479, and 09/232,478 and to the concurrently filed application of Rijsewijk et al. Ser. No. 09/232,469. All of the above-mentioned applications, as well as all documents cited herein and documents referenced or cited in documents cited herein, are hereby incorporated herein by reference. Vectors of vaccines or immunological compositions of the aforementioned applications, as well as of documents cited herein or documents referenced or cited in documents cited herein or portions of such vectors (e.g., one or more or all of regulatory sequences such as DNA for promoter, leader for secretion, terminator), may to the extent practicable with respect to the preferred host of this application, also be employed in the practice of this invention; and, DNA for vectors of vaccines or immunological compositions herein can be obtained from available sources and knowledge in the art, e.g., GeneBank, such that from this disclosure, no undue experimentation is required to make or use such vectors.

The present invention relates to a vaccine formula allowing the vaccination of cats against a number of pathologies. It also relates to a corresponding method of vaccination.

Associations of vaccines against certain canine viruses have already been proposed in the past.

The associations developed so far were prepared from inactivated vaccines or live vaccines and, optionally, mixtures of such vaccines. Their development poses problems of compatibility between valencies and of stability. It is indeed necessary to ensure both the compatibility between the different vaccine valencies, whether from the point of view of the different antigens used or from the point of view of the formulations themselves, especially in the case where both inactivated vaccines and live vaccines are combined. The problem of the conservation of such combined vaccines and of their safety especially in the presence of an adjuvant also exists. These vaccines are in general quite expensive.

Patent Applications WO-A-90 11092, WO-A-93 19183, WO-A-94 21797 and WO-A-95 20660 have made use of the recently developed technique of polynucleotide vaccines. It is known that these vaccines use a plasmid capable of expressing, in the host cells, the antigen inserted into the plasmid. All the routes of administration have been proposed (intraperitoneal, intravenous, intramuscular, transcutaneous, intradermal, mucosal and the like). Various vaccination means can also be used, such as DNA deposited at the surface of gold particles and projected so as to penetrate into the animals' skin (Tang et al., Nature 356, 152–154, 1992) and liquid jet injectors which make it possible to transfect at the same time the skin, the muscle, the fatty tissues and the mammary tissues (Furth et al., Analytical Biochemistry, 205, 365–368, 1992).

(See also U.S. Pat. Nos. 846,946, 5,620,896, 5,643,578, 5,580,589, 5,589,466, 5,693,622, and 5,703,055; Science, 259:1745–49, 1993; Robinson et al., seminars in IMMUNOLOGY, 9:271–83, 1997; Luke et al., J. Infect. Dis. 175(1):91–97, 1997; Norman et al., Vaccine, 15(8):801–803, 1997; Bourne et al., The Journal of Infectious Disease, 173:800–7, 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.)

The polynucleotide vaccines may also use both naked DNAs and DNAs formulated, for example, inside cationic lipids or liposomes.

The invention therefore proposes to provide a multivalent vaccine formula which makes it possible to ensure vaccination against a number of feline pathogenic viruses.

Another objective of the invention is to provide such a vaccine formula combining different valencies while exhibiting all the criteria required for mutual compatibility and stability of the valencies.

Another objective of the invention is to provide such a vaccine formula which makes it possible to combine different valencies in the same vehicle.

Another objective of the invention is to provide such a vaccine which is easy and inexpensive to use.

Yet another objective of the invention is to provide a method for vaccinating cats which makes it possible to obtain protection, including multivalent protection, with a high level of efficiency and of long duration, as well as good safety.

The subject of the present invention is therefore a vaccine formula intended for cats, comprising at least three polynucleotide vaccine valencies each comprising a plasmid integrating, so as to express it in vivo in the host cells, a gene with one feline pathogen valency, these valencies being selected from those of the group consisting of feline leukaemia virus (FeLV), panleukopenia virus (FPV), infectious peritonitis virus (FIPV), coryza virus (FHV), calicivirosis virus (FCV), feline immunodeficiency virus (FIV) and possibly rabies virus (rhabdovirus), the plasmids comprising, for each valency, one or more of the genes selected from the group consisting of env and gag/pol for the feline leukaemia, VP2 for the panleukopenia, modified S (or S*) and M for the infectious peritonitis, gB and gD for the coryza, capsid for the calicivirosis, env and gag/pro for the feline immunodeficiency and G for the rabies.

Valency in the present invention is understood to mean at least one antigen providing protection against the virus for the pathogen considered, it being possible for the valency to contain, as subvalency, one or more modified or natural genes from one or more strains of the pathogen considered.

Pathogenic agent gene is understood to mean not only the complete gene but also the various nucleotide sequences, including fragments which retain the capacity to induce a protective response. The notion of a gene covers the nucleotide sequences equivalent to those described precisely in the examples, that is to say the sequences which are different but which encode the same protein. It also covers the nucleotide sequences of other strains of the pathogen considered, which provide cross-protection or a protection specific for a strain or for a strain group. It also covers the nucleotide sequences which have been modified in order to facilitate the in vivo expression by the host animal but encoding the same protein.

Preferably, the vaccine formula according to the invention comprises the panleukopenia, coryza and calicivirosis valencies.

It will be possible to add the feline leukaemia, feline immunodeficiency and/or infectious peritonitis valencies.

As regards the coryza valency, it is preferable to use the two genes coding for gB and gD, in different plasmids or in one and the same plasmid, or to use either of these genes.

For the feline leukaemia valency, use is preferably made of the two env and gag/pol genes integrated into two different plasmids or into one and the same plasmid, or the env gene alone.

For the feline immunodeficiency valency, use will preferably be made of the two env and gag/pro genes in different plasmids or in one and the same plasmid, or only one of these genes. Still more preferably, the FeLV-A env gene and the FeLV-A and FeLV-B env genes are used.

For the infectious peritonitis valency, use is preferably made of the two M and modified S genes together in two different plasmids or in one and the same plasmid, or either of these genes. S will be modified in order to make the major facilitating epitopes inactive, preferably according to the teaching of Patent PCT/FR95/01128.

The vaccine formula according to the invention can be presented in a dose volume of between 0.1 and 3 ml and in particular between 0.5 and 1 ml.

The dose will be generally between 10 ng and 1 mg, preferably between 100 ng and 500 μg and still more preferably between 1 μg and 250 μg per plasmid type.

Use will preferably be made of naked plasmids simply placed in the vaccination vehicle which will be in general physiological saline (0.9% NaCl), ultrapure water, TE buffer and the like. All the polynucleotide vaccine forms described in the prior art can of course be used.

Each plasmid comprises a promoter capable of ensuring the expression of the gene inserted, under its control, into the host cells. This will be in general a strong eukaryotic promoter and in particular a cytomegalovirus early CMV-IE promoter of human or murine origin, or optionally of another origin such as rats, pigs and guinea pigs.

More generally, the promoter may be either of viral origin or of cellular origin. As viral promoter, there may be mentioned the SV40 virus early or late promoter or the Rous sarcoma virus LTR promoter. It may also be a promoter from the virus from which the gene is derived, for example the gene's own promoter.

As cellular promoter, there may be mentioned the promoter of a cytoskeleton gene, such as for example the desmin promoter (Bolmont et al., Journal of Submicroscopic Cytology and Pathology, 1990, 22, 117–122; and Zhenlin et al., Gene, 1989, 78, 243–254), or alternatively the actin promoter.

When several genes are present in the same plasmid, these may be presented in the same transcription unit or in two different units.

The combination of the different vaccine valencies according to the invention may be preferably achieved by mixing the polynucleotide plasmids expressing the antigen (s) of each valency, but it is also possible to envisage causing antigens of several valencies to be expressed by the same plasmid.

The subject of the invention is also monovalent vaccine formulae comprising one or more plasmids encoding one or more genes from one of the viruses above, the genes being those described above. Besides their monovalent character, these formulae may possess the characteristics stated above as regards the choice of the genes, their combinations, the composition of the plasmids, the dose volumes, the doses and the like.

The monovalent vaccine formulae may also be used (i) for the preparation of a polyvalent vaccine formula as described above, (ii) individually against the actual pathology, (iii) combined with a vaccine of another type (live or inactivated whole, recombinant, subunit) against another pathology, or (iv) as booster for a vaccine as described below.

The subject of the present invention is in fact also the use of one or more plasmids according to the invention for the manufacture of a vaccine intended to vaccinate cats first vaccinated by means of a first conventional vaccine (monovalent or multivalent) of the type in the prior art, in particular, selected from the group consisting of a live whole vaccine, an inactivated whole vaccine, a subunit vaccine, a recombinant vaccine, this first vaccine having (that is to say containing or capable of expressing) the antigen(s) encoded by the plasmid(s) or antigen(s) providing cross-protection.

Remarkably, the polynucleotide vaccine has a potent booster effect which results in an amplification of the immune response and the acquisition of a long-lasting immunity.

In general, the first-vaccination vaccines can be selected from commercial vaccines available from various veterinary vaccine producers.

The subject of the invention is also a vaccination kit grouping together a first-vaccination vaccine as described above and a vaccine formula according to the invention for the booster. It also relates to a vaccine formula according to the invention accompanied by a leaflet indicating the use of this formula as a booster for a first vaccination as described above.

The subject of the present invention is also a method for vaccinating cats, comprising the administration of an effective vaccine formula as described above. This vaccination method comprises the administration of one or more doses of the vaccine formula, it being possible for these doses to be administered in succession over a short period of time and/or in succession at widely spaced intervals.

The vaccine formulae according to the invention can be administered in the context of this method of vaccination, by the different routes of administration proposed in the prior art for polynucleotide vaccination and by means of known techniques of administration.

The subject of the invention is also the method of vaccination consisting in making a first vaccination as described above and a booster with a vaccine formula according to the invention.

In a preferred embodiment of the process according to the invention, there is administered in a first instance, to the animal, an effective dose of the vaccine of the conventional, especially inactivated, live, attenuated or recombinant, type, or alternatively a subunit vaccine, so as to provide a first vaccination, and, after a period preferably of 2 to 6 weeks, the polyvalent or monovalent vaccine according to the invention is administered.

The efficiency of presentation of the antigens to the immune system varies according to the tissues. In particular, the mucous membranes of the respiratory tree serve as barrier to the entry of pathogens and are associated with lymphoid tissues which support local immunity. The administration of a vaccine by contact with the mucous membranes, in particular the buccal mucous membrane, the pharyngeal mucous membrane and the mucous membrane of the bronchial region is certainly of interest for vaccination against respiratory and digestive pathologies.

Consequently, the mucosal routes of administration form part of a preferred mode of administration for the invention, using in particular nebulization or spray or drinking water. It will be possible to apply the vaccine formulae and the vaccination methods according to the invention in this context.

The invention also relates to the method of preparing the vaccine formulae, namely the preparation of the valencies and mixtures thereof, as evident from this description.

The invention will now be described in greater detail with the aid of the embodiments of the invention taken with reference to the accompanying drawings.

BRIEF DESCRIPTION OF THE DRAWINGS

FIG. No. 1: Plasmid pVR1012
FIG. No. 2: Plasmid pPB179
FIG. No. 3: Sequence of the FOLV-B env gone
FIG. No. 4: Plasmid pPB180

FIG. No. 5: Sequence of the FeLV-A virus gag/pol gene (Glasgow-1 strain)

FIG. No. 6: Plasmid pPB181

FIG. No. 7: Plasmid pAB009

FIG. No. 8: Plasmid pAB053

FIG. No. 9: Plasmid pAB052

FIG. No. 10: Plasmid pAB056

FIG. No. 11: Plasmid pAB028

FIG. No. 12: Plasmid pAB029

FIG. No. 13: Plasmid pAB010

FIG. No. 14: Plasmid pAB030

FIG. No. 15: Plasmid pAB083

FIG. No. 16: Plasmid pAB041

Sequence listing SEQ ID No.

SEQ ID No. 1: Oligonucleotide PB247

SEQ ID No. 2: Oligonucleotide PB249

SEQ ID No. 3: Oligonucleotide PB281

SEQ ID No. 4: Oligonucleotide PB282

SEQ ID No. 5: Sequence of the FELV-B virus env gene

SEQ ID No. 6: Oligonucleotide PB283

SEQ ID No. 7: Oligonuclootide PB284

SEQ ID No. 8: Sequence of the FeLV-A virus gag/pol gene (Glasgow-1 strain)

SEQ ID No. 9: Oligonucleotide AB021

SEQ ID No. 10: Oligonucleotide AB024

SEQ ID No. 11: Oligonucleotide AB103

SEQ ID No. 12: Oligonucleotide AB112

SEQ ID No. 13: Oligonucleotide AB113

SEQ ID No. 14: Oligonucleotide AB104

SEQ ID No. 15: Oligonucleotide AB101

SEQ ID No. 16: Oligonucleotide AB102

SEQ ID No. 17: Oligonuclootide AB106

SEQ ID No. 18: Oligonucleotide AB107

SEQ ID No. 19: Oligonucleotide AB061

SEQ ID No. 20: Oligonucleotide AB064

SEQ ID No. 21: Oligonucleotide AB065

SEQ ID No. 22: Oligonuclootide AB066

SEQ ID No. 23: Oligonucleotide AB025

SEQ ID No. 24: Oligonucleotide AB026

SEQ ID No. 25: Oligonucleotide AB067

SEQ ID No. 26: Oligonucleotide AB070

SEQ ID No. 27: Oligonucleotide AB154

SEQ ID No. 28: Oligonucleotide AB155

SEQ ID No. 29: Oligonucleotide AB011

SEQ ID No. 30: Oligonucleotide AB012

EXAMPLES

Example 1

Culture of the Viruses

The viruses are cultured on the appropriate cellular system until a cytopathic effect is obtained. The cellular systems to be used for each virus are well known to persons skilled in the art. Briefly, the cells sensitive to the virus used, which are cultured in Eagle's minimum essential medium (MEM medium) or another appropriate medium, are inoculated with the viral strain studied using a multiplicity of infection of 1. The infected cells are then incubated at 37° C. for the time necessary for the appearance of a complete cytopathic effect (on average 36 hours).

Example 2

Extraction of the Viral Genomic DNAs

After culturing, the supernatant and the lysed cells are harvested and the entire viral suspension is centrifuged at 1000 g for 10 minutes at +4° C. so as to remove the cellular debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 $\mu$g/ml final) in the presence of sodium dodecyl sulphate (SDS) (0.5% final) for 2 hours at 37° C. The viral DNA is then extracted with a phenol/chloroform mixture and then precipitated with 2 volumes of absolute ethanol. After leaving overnight at −20° C., the DNA is centrifuged at 10,000 g for 15 minutes at +4° C. The DNA pellet is dried and then taken up in a minimum volume of sterile ultrapure water. It can then be digested with restriction enzymes.

Example 3

Isolation of the Viral Genamic RNAs

The RNA viruses were purified according to techniques well known to persons skilled in the art. The genomic viral RNA of each virus was then isolated using the "guanidium thiocyanate/phenol-chloroform" extraction technique described by P. Chomczynski and N. Sacchi (Anal. Biochem., 1987, 162, 156–159).

Example 4

Molecular Biology Techniques

All the constructions of plasmids were carried out using the standard molecular biology techniques described by J. Sambrook et al. (*Molecular Cloning: A Laboratory Manual*, 2nd Edition, Cold Spring Harbor Laboratory, Cold Spring Harbor, N.Y., 1989). All the restriction fragments used for the present invention were isolated using the "Geneclean" kit (BIO 101 Inc. La Jolla, Calif.).

Example 5

RT-PCR Technique

Specific oligonucleotides (comprising restriction sites at their 5' ends to facilitate the cloning of the amplified fragments) were synthesized such that they completely cover the coding regions of the genes which are to be amplified (see specific examples). The reverse transcription (RT) reaction and the polymerase chain reaction (PCR) were carried out according to standard techniques (Sambrook J. et al., 1989). Each RT-PCR reaction was performed with a pair of specific amplimers and taking, as template, the viral genomic RNA extracted. The complementary DNA amplified was extracted with phenol/chloroform/isoamyl alcohol (25:24:1) before being digested with restriction enzymes.

Example 6

Plasmid pVR1012

The plasmid pVR1012 (FIG. No. 1) was obtained from Vical Inc., San Diego, Calif., USA. Its construction has been

Example 7

Figure 1:
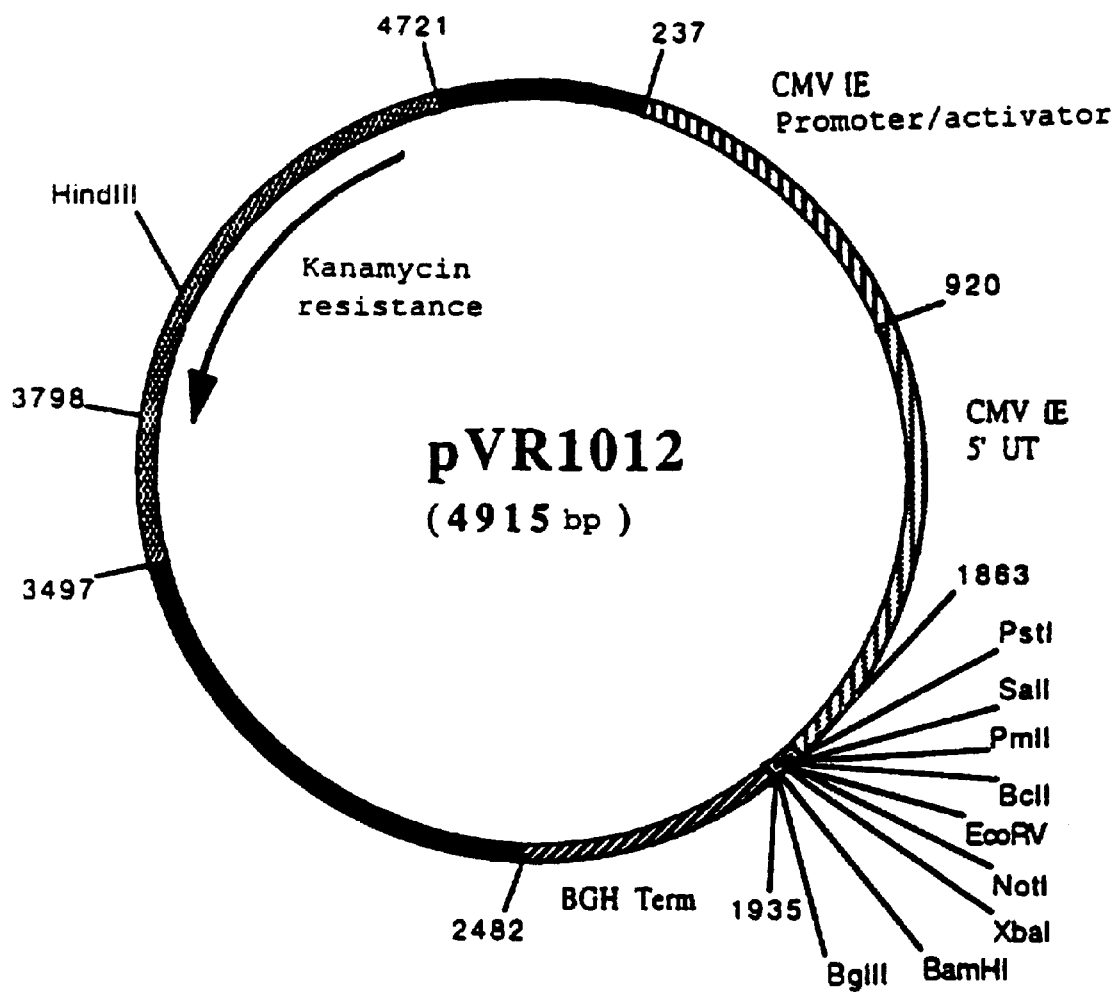
Figure 2:
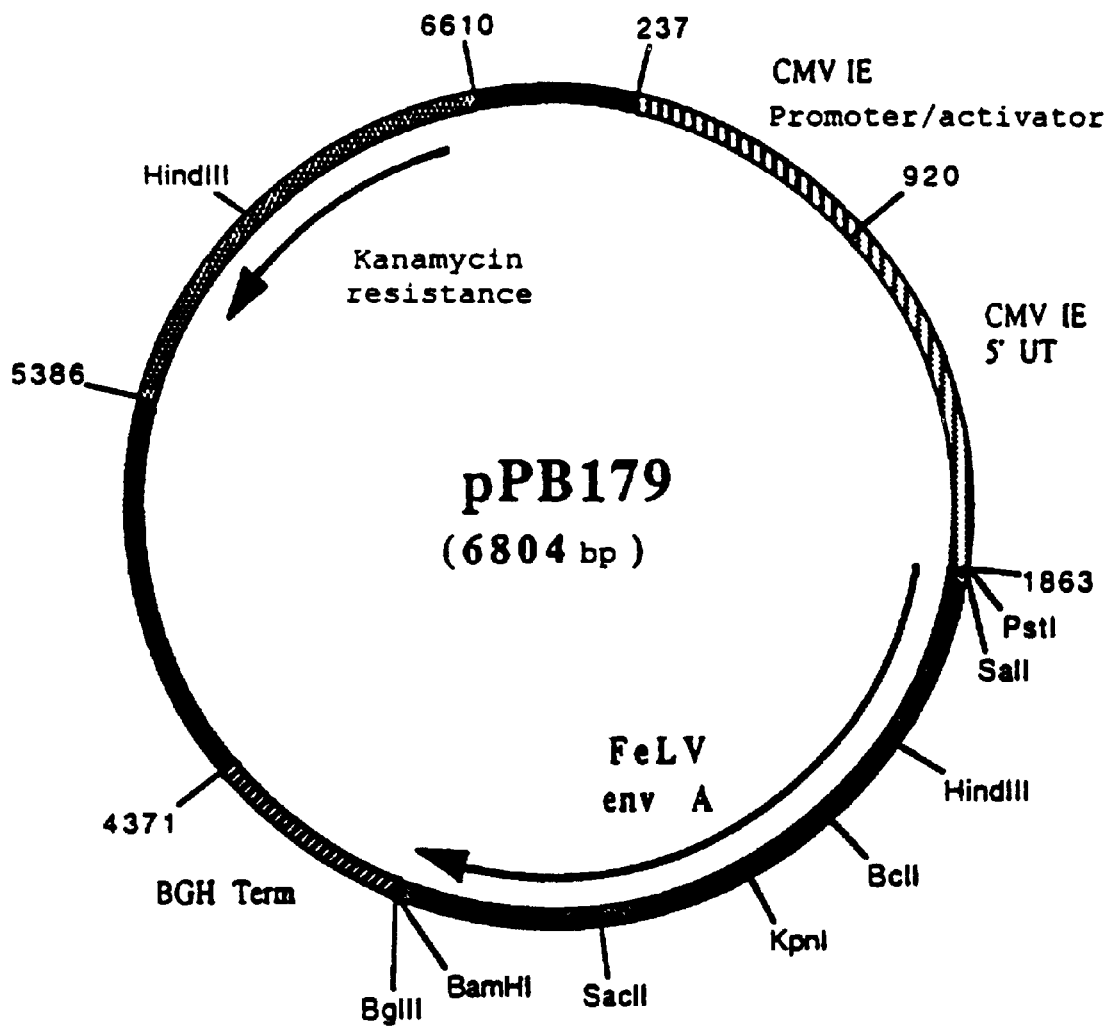
Figure 4:
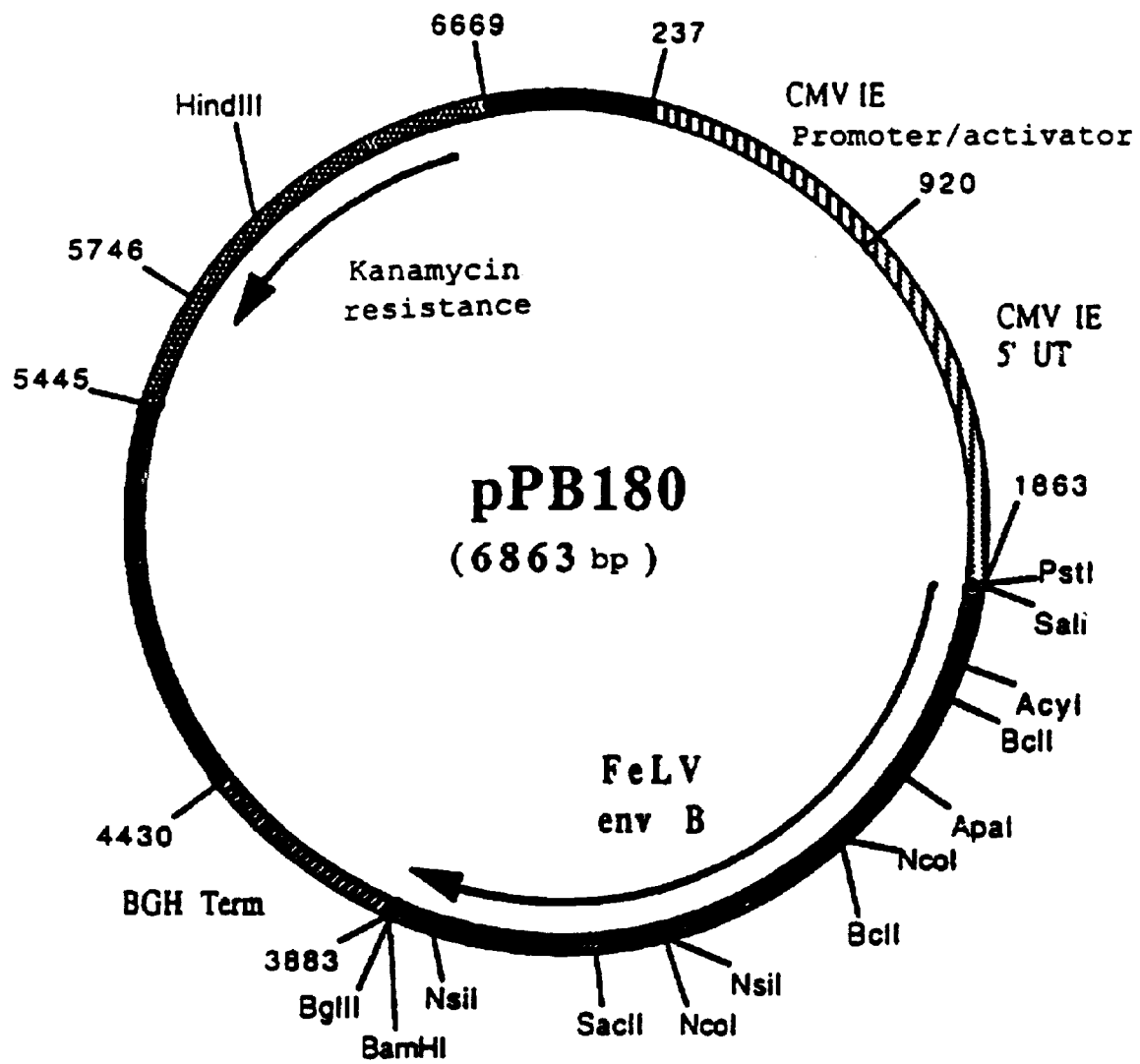
Figure 6:
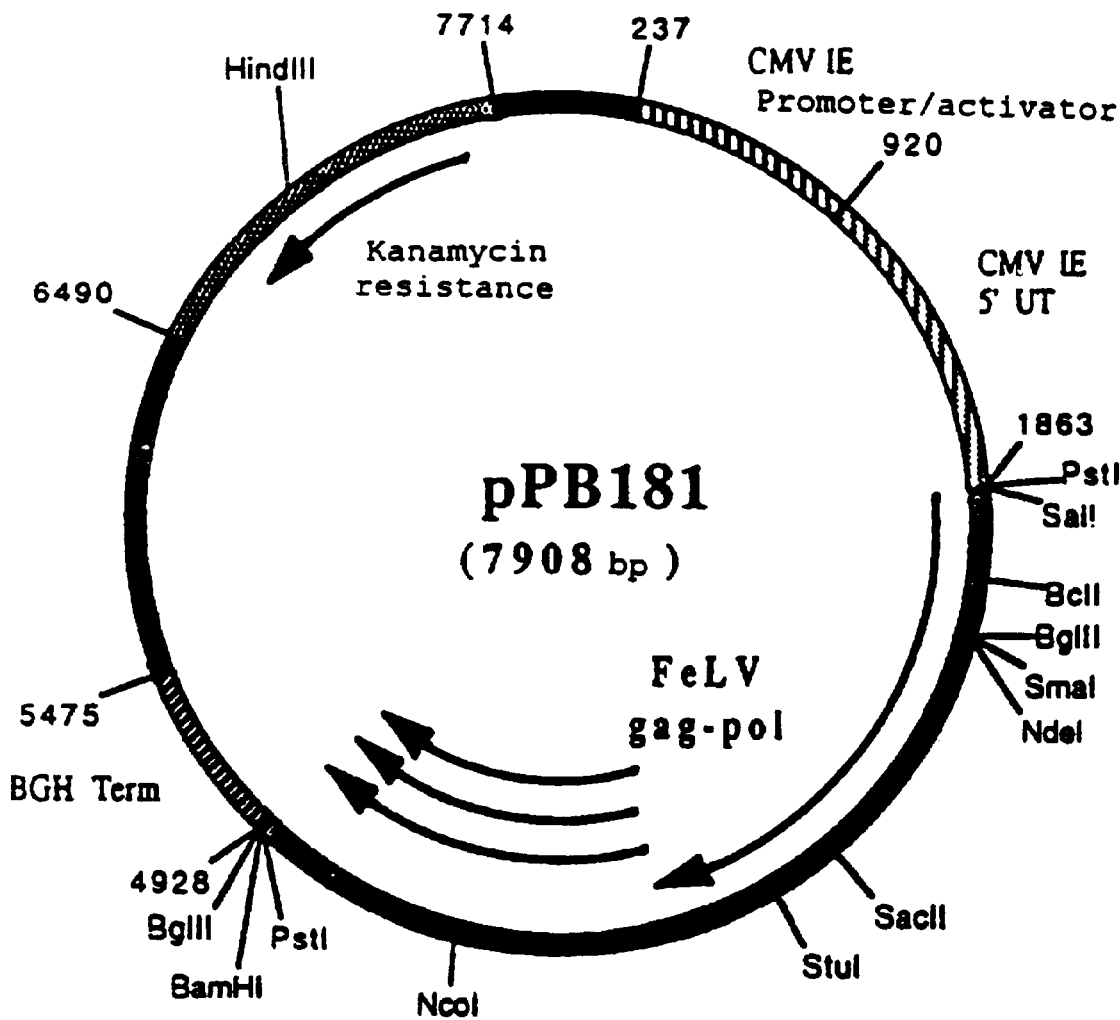
Figure 7:
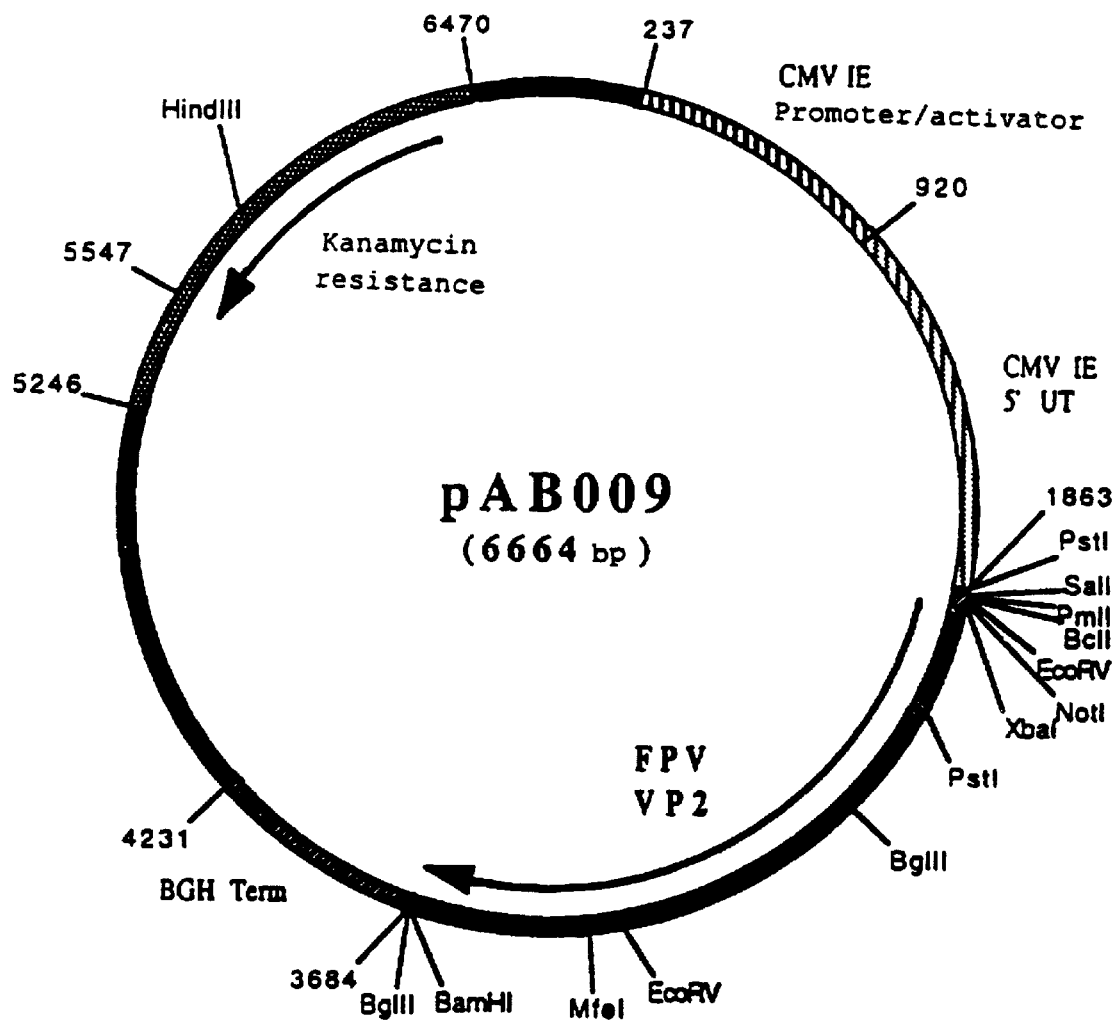
Figure 8:
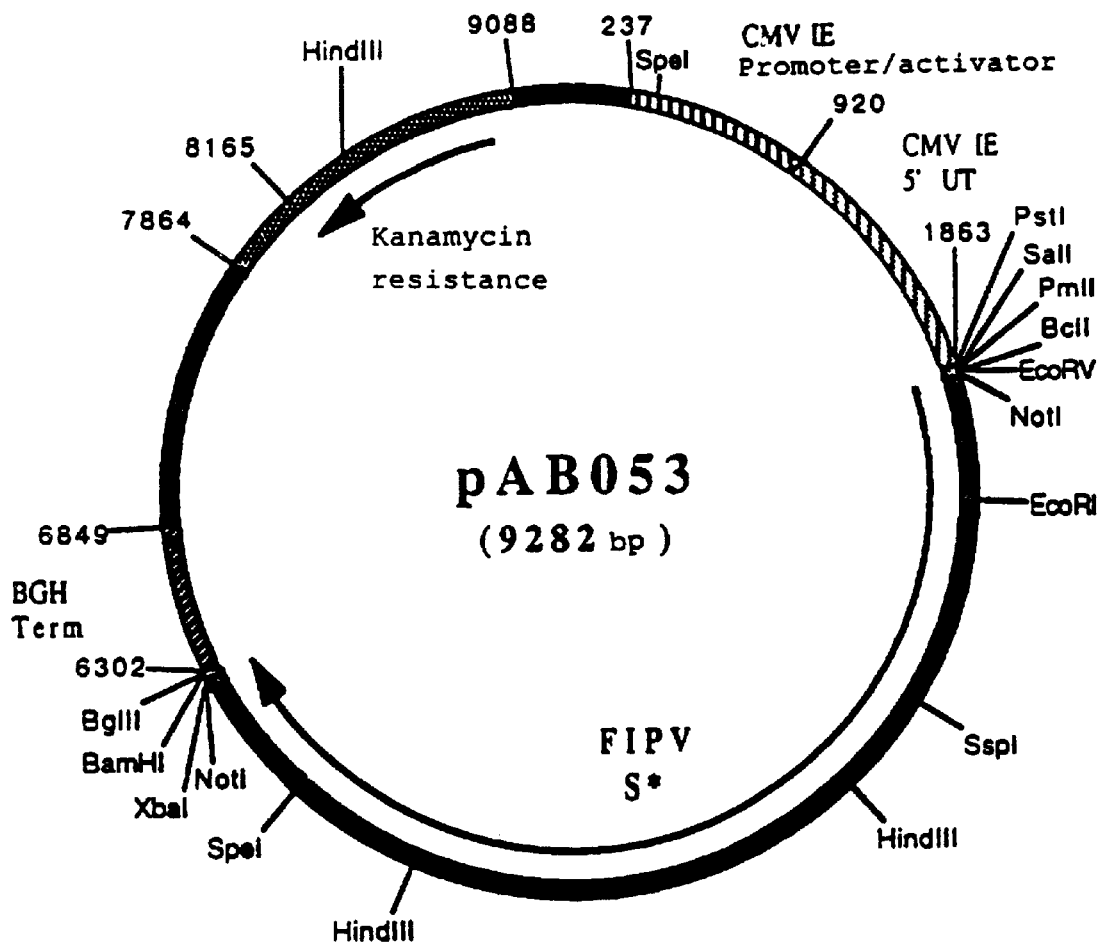
Figure 9:
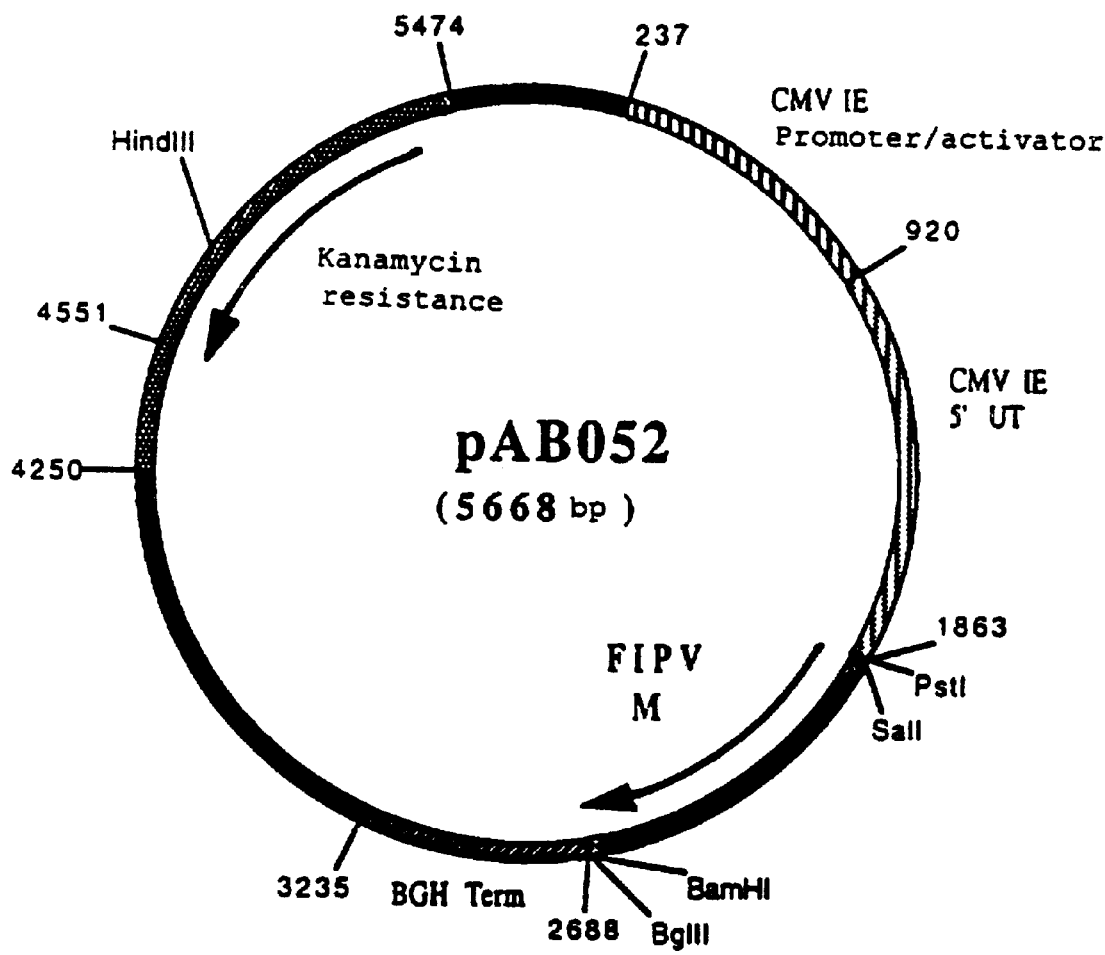
Figure 10:
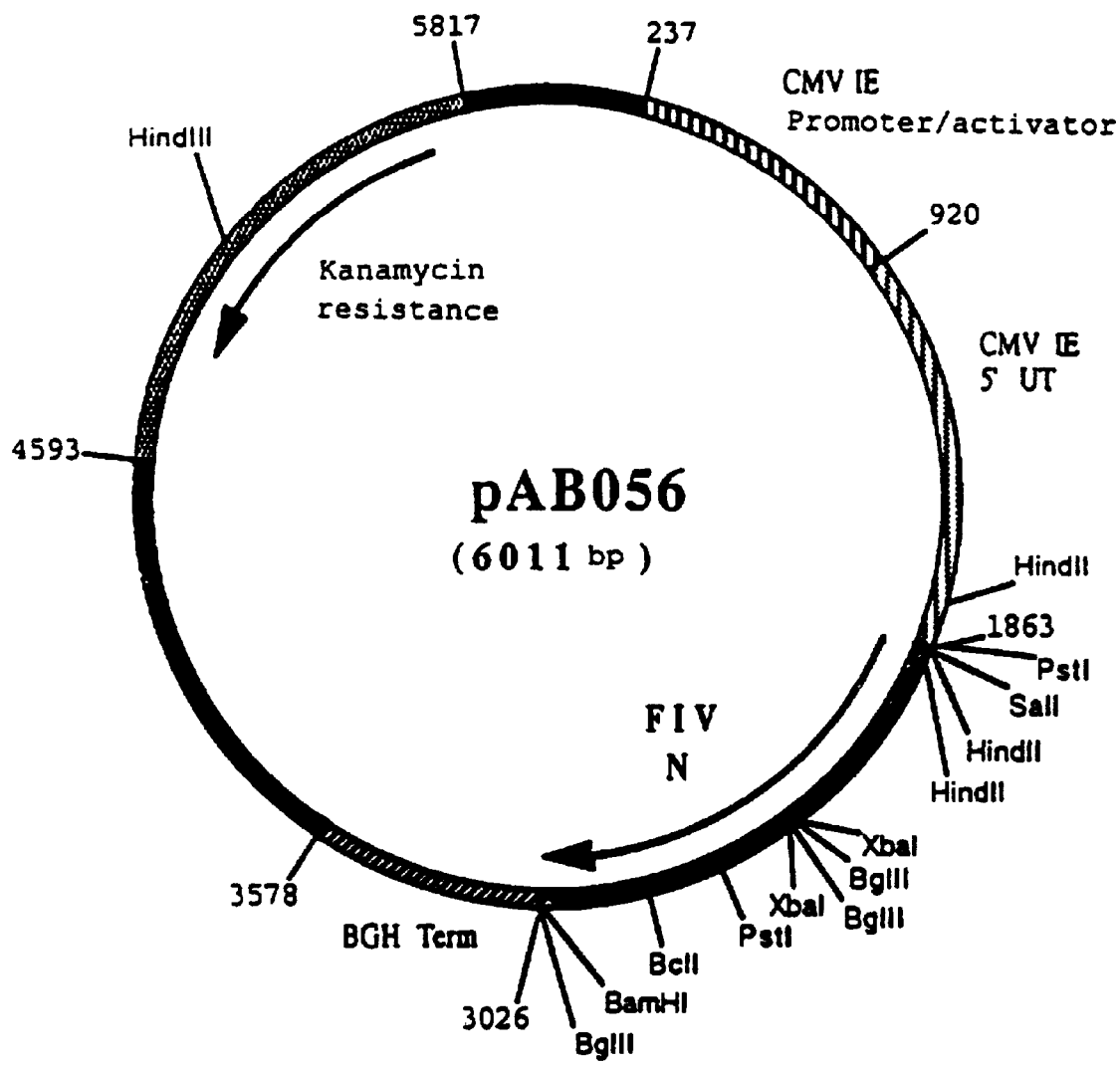
Figure 11:
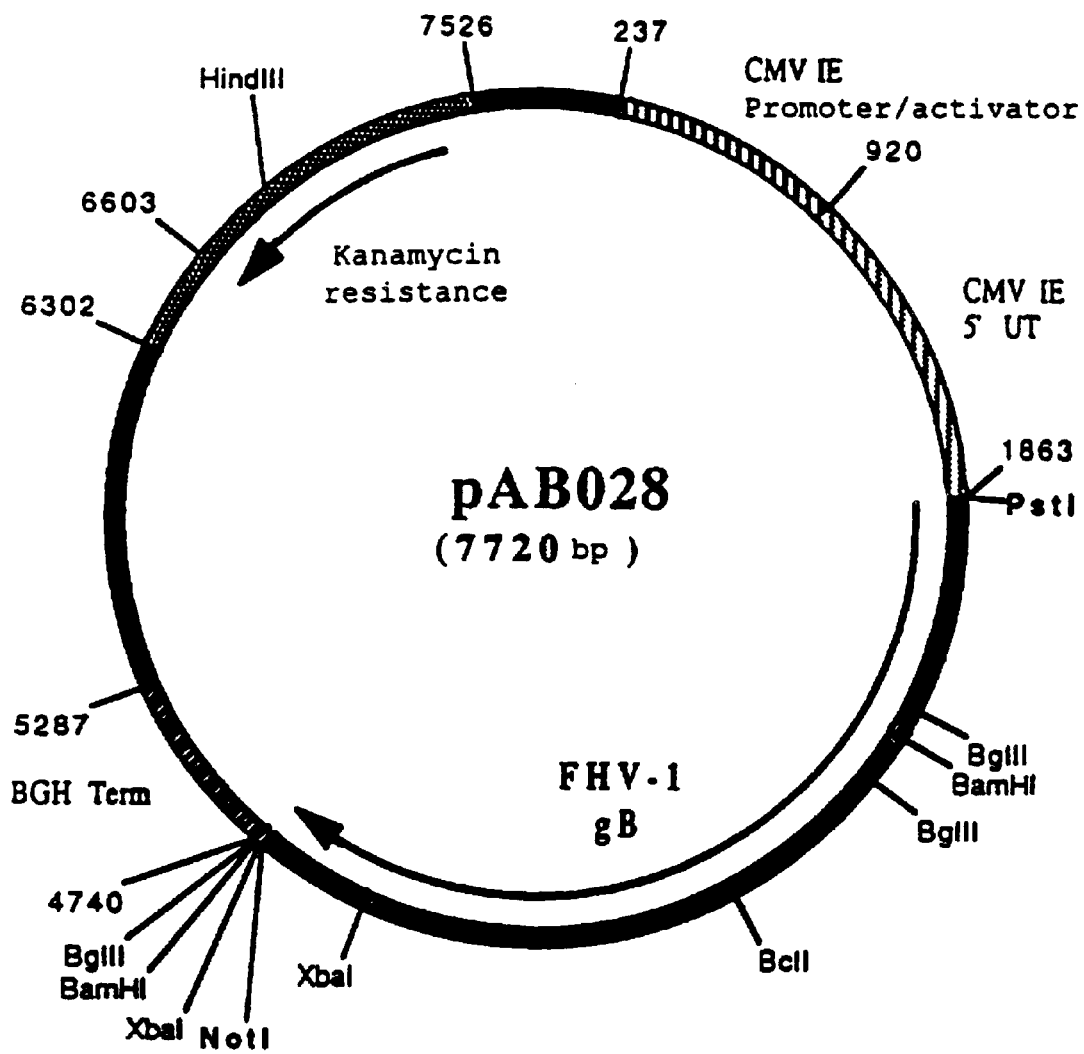
Figure 12:
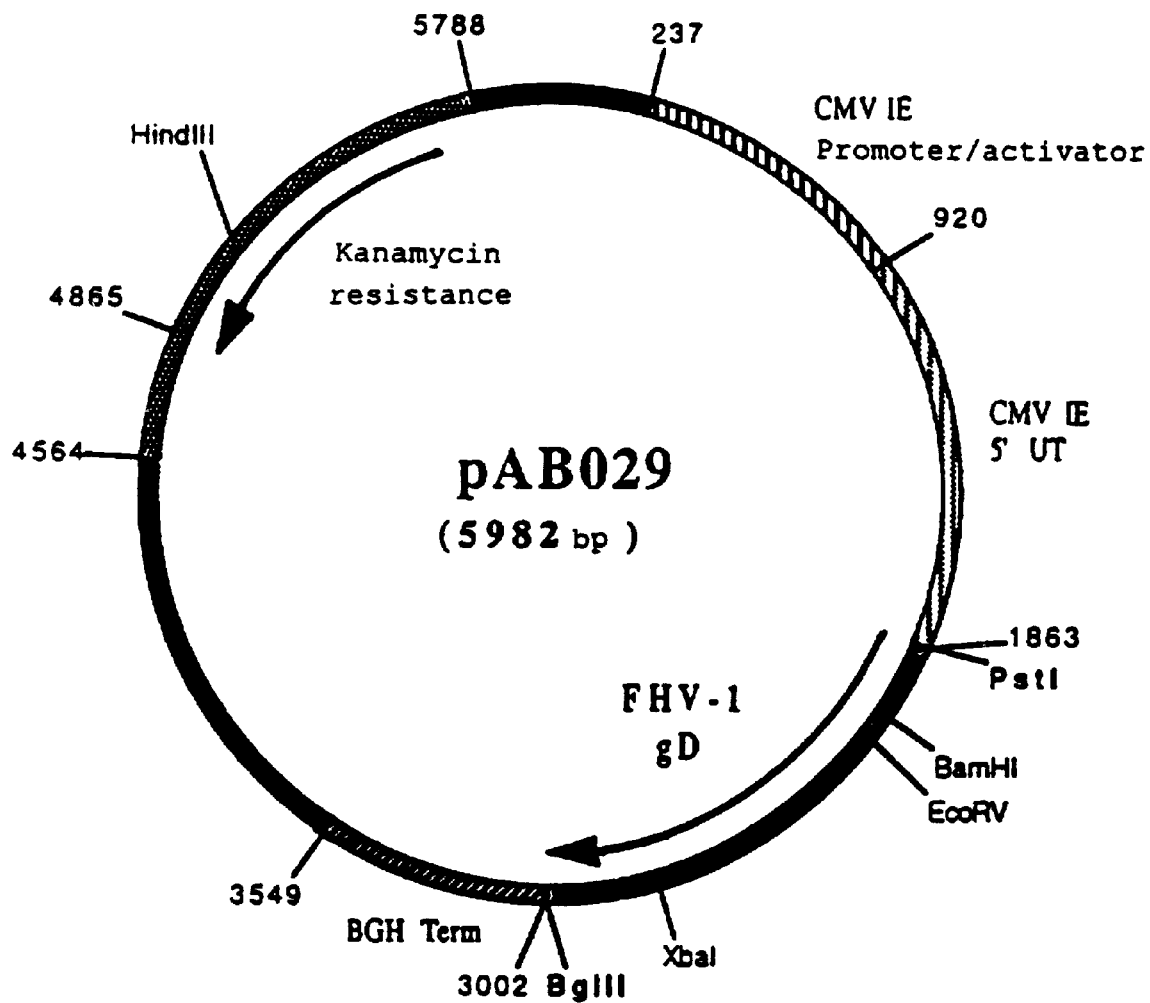
Figure 13:
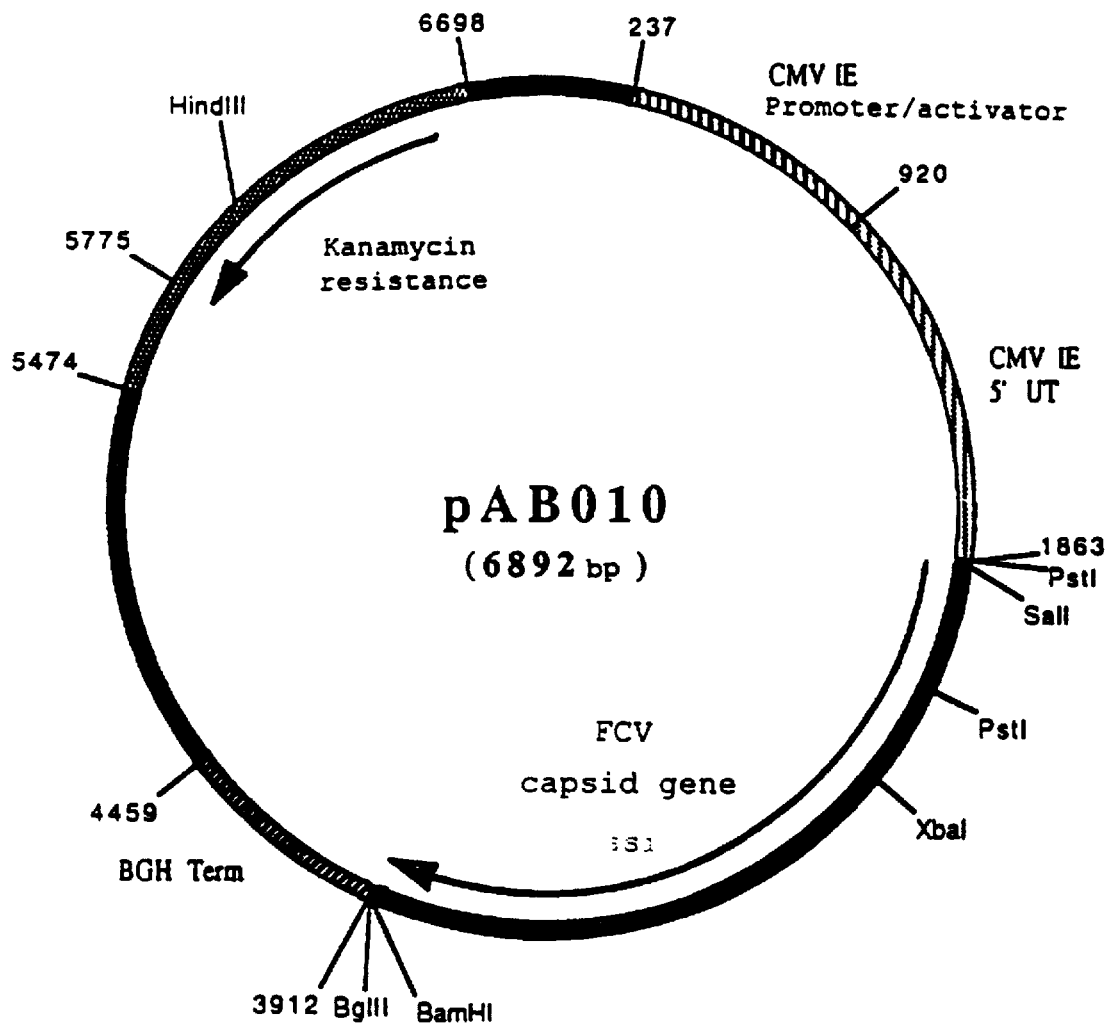
Figure 14:
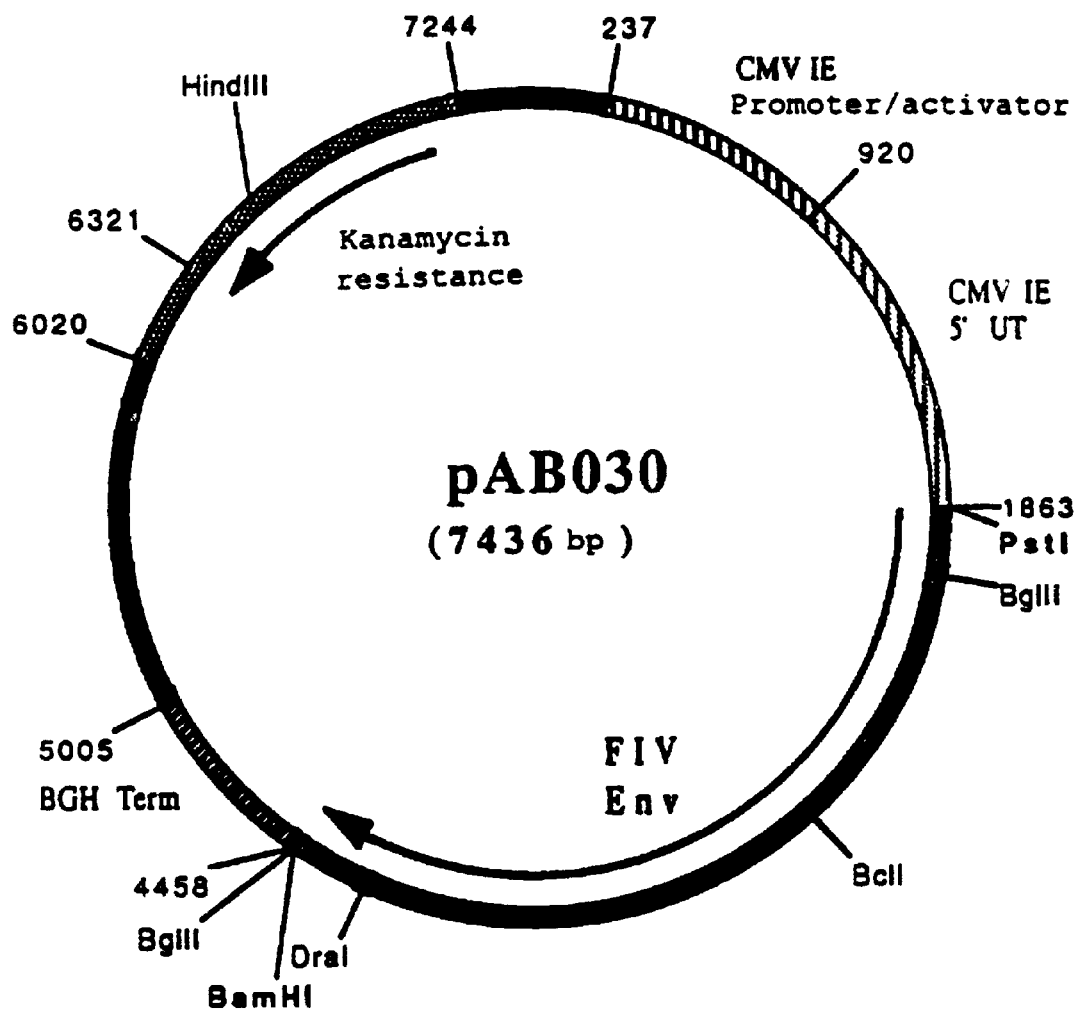
Figure 15:
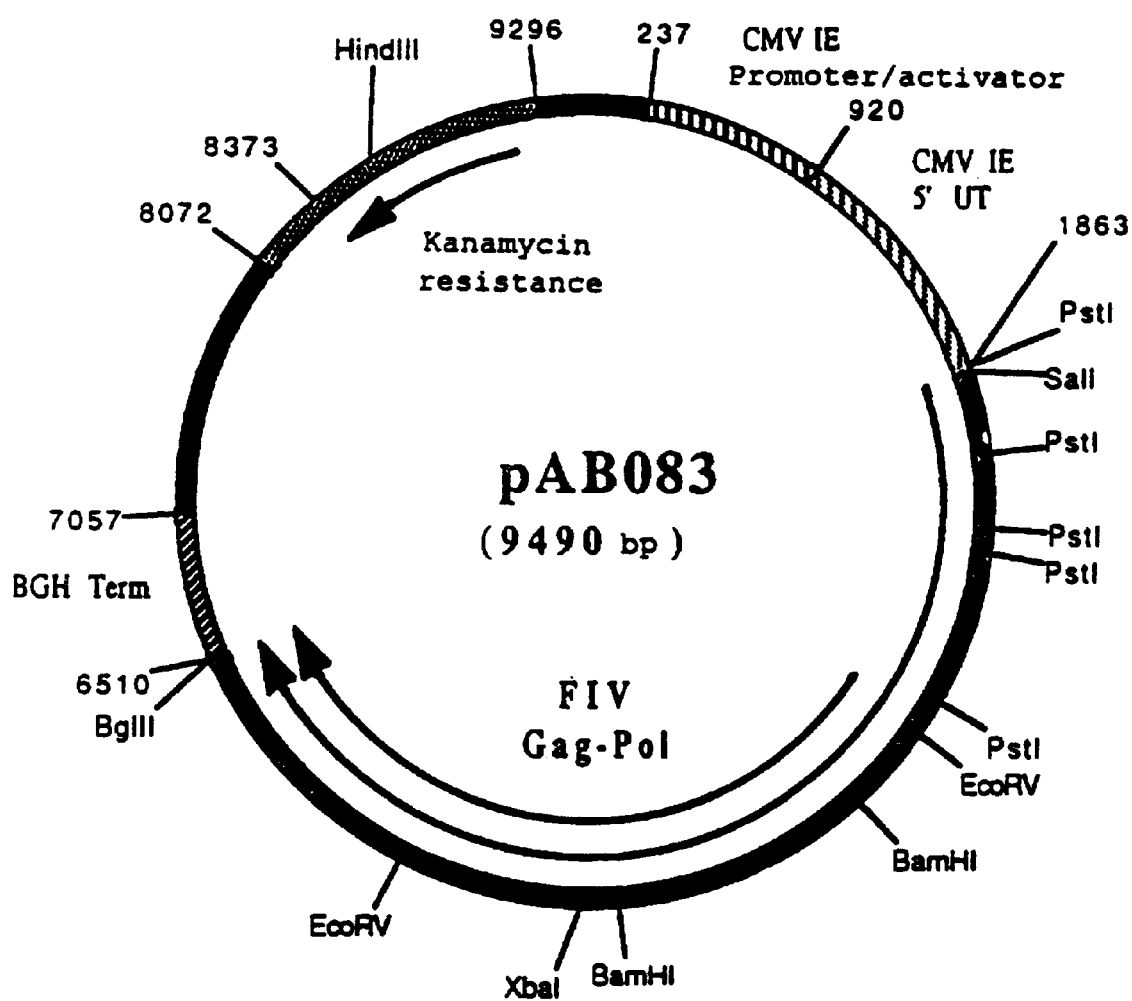
Figure 16:
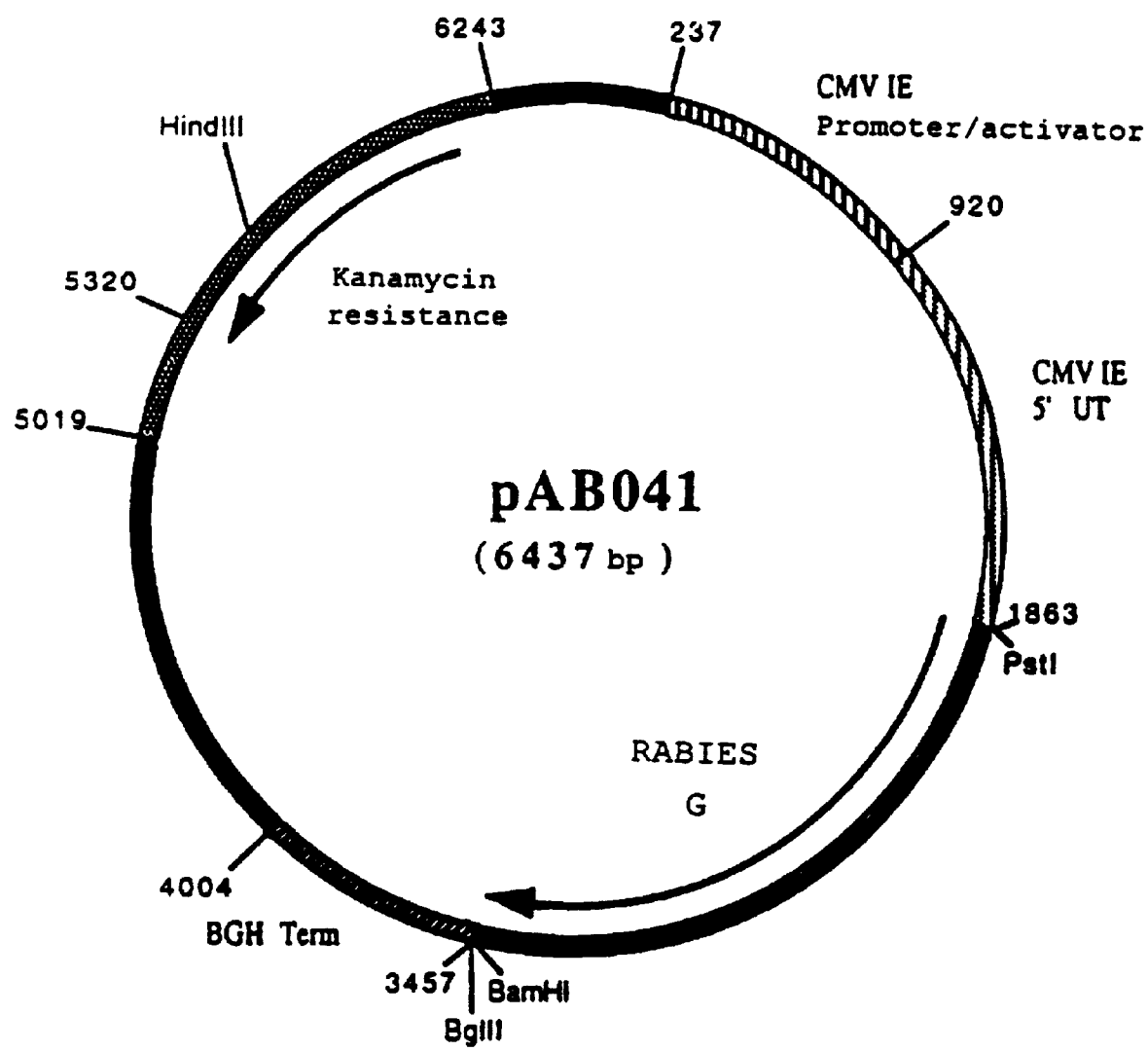

Construction of the Plasmid pPB179 (FeLV-A Virus Env Gene)

An RT-PCR reaction according to the technique of Example 5 was carried out with feline leukaemia virus (FeLV-A) (Glasgow-1 strain) genomic RNA (M. Stewart et al. J. Virol. 1986. 58. 825–834), prepared according to the technique of Example 3, and with the following oligonucleotides:

PB247 (29 mer) (SEQ ID No. 1)
5'TTTGTCGACCATGGAAAGTCCAACGCACC3'
PB249 (28 mer) (SEQ ID No. 2)
5'TTTGGATCCTCATGGTCGGTCCGGATCG3' so as to amplify a 1947 bp fragment containing the gene encoding the Env glycoprotein from the FeLV-A virus (Glasgow-1 strain) in the form of a SalI-BamHI fragment. After purification, the RT-PCR product was digested with SalI and BamHI in order to give a 1935 bp SalI-BamHI fragment.

This fragment was ligated with the vector pVR1012 (Example 6), previously digested with SalI and BamHI, to give the plasmid pPB179 (6804 bp) (FIG. No. 2).

Example 8

Construction of the Plasmid pPB180 (FeLV-S Virus Env Gene)

An RT-PCR reaction according to the technique of Example 5 was carried out with feline leukaemia virus (FeLV-B subtype) genomic RNA, prepared according to the technique of Example 3, and with the following oligonucleotides:

PB281 (29 mer) (SEQ ID No. 3)
5'TTTGTCGACATGGAAGGTCCAACGCACCC3'
PB282 (32 mer) (SEQ ID No. 4)
5'TTGGATCCTCATGGTCGGTCCGGATCATATTG3' so as to amplify a 2005 bp fragment containing the gene encoding the Env glycoprotein from the FeLV-B virus (FIG. No. 3 and SEQ ID No. 5) in the form of a SalI-BamHI fragment. After purification, the RT-PCR product was digested with SalI and BamHI in order to give a 1995 bp SalI-BamHI fragment.

This fragment was ligated with the vector pVR1012 (Example 6), previously digested with SalI and BamHI, to give the plasmid pPB180 (6863 bp) (FIG. No. 4).

Example 9

Construction of the Plasmid pPB181 (FeLV gag/pol gene)

An RT-PCR reaction according to the technique of Example 5 was carried out with the feline leukaemia virus (FeLV-A subtype) (Glasgow-1 strain) genomic RNA, prepared according to the technique of Example 3, and with the following oligonucleotides:

PB283 (33 mer) (SEQ ID No. 6)
5'TTGTCGACATGTCTGGAGCCTCTAGTGGGACAG3'
PB284 (42 mer) (SEQ ID No. 7)
5'TTGGATCCTTATTTAATTACTGCAGTTCCAAGGAACTCTC3' so as to amplify a 3049 bp fragment containing the sequence encoding the Gag protein and the 5' part of the sequence encoding the Pol protein from the FeLV-A virus (Glasgow-1 strain) (FIG. No. 5 and SEQ ID No. 8) in the form of a SalI-BamHI fragment. After purification, the RT-PCR product was digested with SalI and BamHI to give a 3039 bp SalI-BamHI fragment.

This fragment was ligated with the vector pVR1012 (Example 6), previously digested with SalI and BamHI, to give the plasmid pPB181 (7908 bp) (Figure No. 6).

Example 10

Construction of the Plasmid pAB009 (FPV VP2 gene)

A PCR reaction was carried out with the feline panleukopaenia virus (193 strain) genomic DNA (J. Martyn et al., J. Gen. Virol. 1990, 71. 2747–2753), prepared according to the technique of Example 2, and with the following oligonucleotides: AB021 (34 mer) (SEQ ID No. 9)

5'TGCTCTAGAGCAATGAGTGATGGAAGCAGTTCAAC3'
AB024 (33 mer) (SEQ ID No. 10)
5'CGCGGATCCATTAATATAATTTTCTAGGTGCTA3' so as to amplify a 1776 bp fragment containing the gene encoding the FPV VP2 capsid protein. After purification, the PCR product was digested with XbaI and BamHI in order to give a 1764 bp XbaI-BamHI fragment.

This fragment was ligated with the vector pVR1012 (Example 6), previously digested with XbaI and BamHI, to give the plasmid pAB009 (6664 bp) (FIG. No. 7).

Example 11

Construction of the Plasmid pAB053 (FIPV S* gene)

An RT-PCR reaction according to the technique of Example 5 was carried out with the feline infectious peritonitis (FIP) virus (79-1146 strain) genomic RNA (R. de Groot et al., J. Gen. Virol. 1987. 68. 2639–2646), prepared according to the technique of Example 3, and with the following oligonucleotides:

AB103 (38 mer) (SEQ ID No. 11)
5'ATAAGAATGCGGCCGCATGATTGTGCTCGTAACTTGCC3'
AB112 (25 mer) (SEQ ID No. 12)
5'CGTACATGTGGAATTCCACTGGTTG3' so as to amplify the sequence of the 5' part of the gene encoding the virus S glycoprotein in the form of an NotI-EcoRI fragment. After purification, the 492 bp RT-PCR product was digested with NotI and EcoRI in order to liberate a 467 bp NotI-EcoRI fragment (fragment A).

The plasmid pJCA089 (Patent Application PCT/FR95/01128) was digested with EcoRI and SpeI in order to liberate a 3378 bp fragment containing the central part of the gene encoding the FIP virus modified S glycoprotein (fragment B).

An RT-PCR reaction according to the technique of Example 5 was carried out with the FIP virus (79-1146 strain) genomic RNA, prepared according to the technique of Example 3, and with the following oligonucleotides:

AB113 (25 mer) (SEQ ID No. 13)

5'AGAGTTGCAACTAGTTCTGATTTTG3'

AB104 (37 mer) (SEQ ID No. 14)

5'ATAAGAATGCGGCCGCTTAGTGGACATG-CACTTTTTC3' so as to amplify the sequence of the 3' part of the gene encoding the FIP virus S glycoprotein in the form of an SpeI-NotI fragment. After purification, the 543 bp RT-PCR product was digested with SpeI and NotI in order to liberate a 519 bp SpeI-NotI fragment (fragment C).

The fragments A, B and C were then ligated together into the vector pVR1012 (Example 6), previously digested with NotI, to give the plasmid pAB053 (9282 bp), which contains the modified S gene in the correct orientation relative to the promoter (FIG. No. 8).

Example 12

Construction of the Plasmid pAB052 (FIPV M gene)

An RT-PCR reaction according to the technique of Example 5 was carried out with the feline infectious peritonitis (FIP) virus (79-1146 strain) genomic RNA (H. Vennema et al., Virology. 1991, 181. 327–335), prepared according to the technique of Example 3, and with the following oligonucleotides:

AB101 (37 mer) (SEQ ID No. 15)

5'ACGCGTCGACCCACCATGAAGTA-CATTTTGCTAATAC3'

AB102 (36 mer) (SEQ ID No. 16)

5'CGCGGATCCTTACACCATATG-TAATAATTTTTCATG3' so as to precisely isolate the gene encoding the FIP virus M glycoprotein in the form of a SalI-BamHI fragment. After purification, the 812 bp RT-PCR product was digested with SalI and BamHI in order to liberate a 799 bp SalI-BamHI fragment. This fragment was then ligated into the vector pVR1012 (Example 6), previously digested with SalI and BamHI, to give the plasmid pAB052 (5668 bp) (FIG. No. 9).

Example 13

Construction of the Plasmid pAB056 (FIPV N gene)

An RT-PCP reaction according to the technique of Example 5 was carried out with the feline infectious peritonitis (FIP) virus (79-1146 strain) genomic RNA (H. Vennema et ail., Virology. 1991, 181. 327–335), prepared according to the technique of Example 3, and with the following oligonucleotides:

AB106 (35 mer) SEQ ID No. 17)

5'ACGCGTCGACGCCCTGGCCACACAGGGA-CAACGCG3'

AB107 (36 mer) (SEQ ID No. 18)

5'CGCGGATCCTTAGTCGTAACCTCAT-CAATCATCTC3' so as to precisely isolate the gene encoding the FIP virus N protein in the form of a SalI-BamHI fragment. After purification, the 1156 bp RT-PCR product was digested with SalI and BamHI in order to liberate a 1143 bp SalI-BamHI fragment. This fragment was then ligated into the vector pVR1012 (Example 6), previously digested with SalI and BamHI, to give the plasmid pAB056 (6011 bp) (FIG. No. 10).

Example 14

Construction of the Plasma pAB028 (FEV gB gene)

A PCR reaction was carried out with the feline herpesvirus (FHV-1) (C27 strain) genomic DNA (S. Spatz et al. Virology. 1993. 197. 125–36) prepared according to the technique of Example 2, and with the following oligonucleotides:

AB061 (36 mer) (SEQ ID No. 19)

5'AAAACTGCAGAATCATGTCCACTCGTG-GCGATCTTG3'

AB064 (40 mer) (SEQ ID No. 20)

5'ATAAGAATGCGGCCCCTTAGACAA-GATTTGTTTCAGTATC3' so as to amplify a 2856 bp fragment containing the gene encoding the FHV-1 virus gB glycoprotein in the form of a PstI-NotI fragment. After purification, the PCR product was digested with PstI and NotI to give a 2823 bp PstI-NotI fragment.

This fragment was ligated with the vector pVR1012 (Example 6), previously digested with PstI and NotI, to give the plasmid pAB028 (7720 bp) (FIG. No. 11).

Example 15

Construction of the Plasmid pAB029 (FHV gD gene)

A PCR reaction was carried out with the feline herpesvirus (FHV-1) (C-27 strain) genomic DNA (S. Spatz et al. J. Gen. Virol. 1994. 75. 1235–1244), prepared according to the technique of Example 2 and with the following oligonucleotides:

AB065 (36 mer) (SEQ ID No. 21)

5'AAAACTGCAGCCATGATGACACGTCTA-CATTTTTG3'

AB066 (33 mer) (SEQ ID No. 22)

5'GGAAGATCTTTAAGGATGGTGAGTTG-TATGTAT3' so as to amplify the gene encoding the FHV-1 virus gD glycoprotein in the form of a PstI-BglII fragment. After purification, the 1147 bp PCR product was digested with PstI and BglII in order to isolate a 1129 bp PstI-BglII fragment. This fragment was ligated with the vector pVR1012 (Example 6), previously digested with PstI and BglII, to give the plasmid pAB029 (5982 bp) (FIG. No. 12).

Example 16

Construction of the Plasmid pAB010 (FCV C gene)

An RT-PCR reaction according to the technique of Example 5 was carried out with the feline calicivirus (FCV) (F9 strain) genomic RNA (M. Carter et al. Virology. 1992. 190. 443–448), prepared according to the technique of Example 3, and with the following oligonucleotides:

AB025 (33 mer) (SEQ ID No. 23)

5'ACGCGTCGACGCATCTGCTCAACCT-GCGCTAAC3'

AB026 (31 mer) (SEQ ID No. 24)

5'CGCGGATCCTCATAACTTAGTCATGGGACTC3' so as to isolate the gene encoding the FCV virus capsid protein in the form of a SalI-BamHI fragment. After purification, the 2042 bp RT-PCR product was digested with SalI and BamHI in order to isolate a 2029 bp SalI-BamHI fragment. This fragment was ligated with the vector PVR1012 (Example 6), previously digested with SalI and BamHI, to give the plasmid pAB010 (6892 bp) (FIG. No. 13).

Example 17

Construction of the Plasmid pAB030 (FIV env gene)

An RT-PCR reaction according to the technique of Example 5 was carried out with the feline immunodeficiency virus (FIV) (Petaluma strain) genomic RNA (R. Olmstec. et al. Proc. Natl. Acad. Sci. USA. 1989. 86. 8083–8096), prepared according to the technique of Example 3, and with the following oligonucleotides:

AB067 (36 mer) (SEQ ID No. 25)
5'AAAACTGCAGAAGGAATGGCAGAAG-GATTTGCAGCC3'
AB070 (36 mer) (SEQ ID No. 26)
5'CGCGGATCCTCATTCCTCCTCTTTTCA-GACATGCC3' so as to amplify a 2592 bp fragment containing the gene encoding the Env glycoprotein from the FIV virus (Petaluma strain, in the form of a PstI-BamHI fragment. After purification, the RT-PCR product was digested with PstI and BamHI to give a 2575 bp PstI-BamHI fragment.

This fragment was ligated with the vector pVR1012 (Example 6), previously digested with PstI and BamHI, to give the plasmid pAB030 (7436 bp) (FIG. No. 14).

Example 18

Construction of the Plasmid pAB083 (FIV gag/pro gene)

An RT-PCR reaction according to the technique of Example 5 was carried out with the feline immunodeficiency virus (FIV) (Petaluma strain) genomic RNA (R. Olmsted et al. Proc. Natl. Acad. Sci. USA. 1989. 86. 8088–8096), prepared according to the technique of Example 3, and with the following oligonucleotides:

AB154 (32 mer) (SEQ ID No. 27)
5'ACGCGTCGACATGGGGAATGGA-CAGGGGCGAG3'
AB155 (33 mer) (SEQ ID No. 28)
5'TGAAGATCTTCACTCATCCCCTTCAG-GAAGAGC3' so as to amplify a 4635 bp fragment containing the gene encoding the Gag and Pro proteins from the FIV virus (Petaluma strain) in the form of a SalI-BglII fragment. After purification, the RT-PCR product was digested with SalI and BglII to give a 4622 bp SalI-BglII fragment.

This fragment was ligated with the vector pVR1012 (Example 6), previously digested with SalI and BglII, to give the plasmid pAB083 (7436 bp) (FIG. No. 15).

Example 19

Construction of the Plasmid pAB041 (rabies virus G gene)

An RT-PC'R reaction according to the technique of Example 5 was carried out with the rabies virus (ERA strain) genomic RNA (A. Anilionis et al. Nature. 1981. 294. 275–278), prepared according to the technique of Example 3, and with the following oligonucleotides:

AB011 (33 mer) (SEQ ID No. 29)
5'AAAACTGCAGAGATGGTTCCTCAG-GCTCTCCTG3'
AB012 (34 mer) (SEQ ID No. 30)
5'CGCGGATCCTCACACTCTGGTCTCAC-CCCCACTC3' so as to amplify a 1589 bp fragment containing the gene encoding the rabies virus G glycoprotein. After purification, the RT-PCR product was digested with PstI and BamHI to give a 1578 bp PstI-BamHI fragment. This fragment was ligated with the vector pVR1012 (Example 6), previously digested with PstI and BamHI, to give the plasmid pAB041 (6437 bp) (FIG. No. 16).

Example 20

Production and Purification of the Plasmids

For the preparation of the plasmids intended for the vaccination of animals, any technique may be used which makes it possible to obtain a suspension of purified plasmids predominantly in the supercoiled form. These techniques are well known to persons skilled in the art. There may be mentioned in particular the alkaline lysis technique followed by two successive ultracentrifugations on a caesium chloride gradient in the presence of ethidium bromide as described in J. Sambrook et al. (*Molecular Cloning: A Laboratory Manual*, 2nd edition, Cold Spring Harbor Laboratory, Cold Spring Harbor, N.Y., 1989). Reference may also be made to Patent Applications PCT WO 95/21250 and PCT WO 96/02658 which describe methods for producing, on an industrial scale, plasmids which can be used for vaccination. For the purposes of the manufacture of vaccines (see Example 17), the purified plasmids are resuspended so as to obtain solutions at a high concentration (>2 mg/ml) which are compatible with storage. To do this the plasmids are resuspended either in ultrapure water or in TE buffer (10 mM Tris-HCl; 1 mM EDTA, pH 8.0).

Example 21

Manufacture of the Associated Vaccines

The various plasmids necessary for the manufacture of an associated vaccine are mixed starting with their concentrated solutions (Example 16). The mixtures are prepared such that the final concentration of each plasmid corresponds to the effective dose of each plasmid. The solutions which can be used to adjust the final concentration of the vaccine may be either a 0.9% NaCl solution, or PBS buffer.

Specific formulations such as liposomes, cationic lipids, may also be used for the manufacture of the vaccines.

Example 22

Vaccination of Cats

The cats are vaccinated with doses of 10 µg, 50 µg or 250 µg per plasmid.

The injections are performed with a needle by the intramuscular route. In this case, the vaccinal doses are administered in a volume of 1 ml.

The injections can also be performed with a needle by the intradermal route. In this case, the vaccinal doses are administered in a total volume of 1 ml administered at 10 points of 0.1 ml or at 20 points of 0.05 ml. The intradermal administrations are performed after shaving the skin (thoracic flank in general) or at the level of a relatively glabrous anatomical region, for example the inner surface of the thigh.

A liquid jet injection apparatus (with no needle) can also be used for the intradermal injections.

What is claimed is:

1. An immunogenic composition for inducing in a feline host an immunological response against infectious peritonitis virus comprising a plasmid that contains and expresses in vivo in a feline host cell a nucleic acid molecule having a sequence encoding infectious peritonitis virus M protein.

2. The immunogenic composition of claim 1 wherein the plasmid further comprises a cytomeglovirus early (CMV-IE) promoter operatively linked to the nucleic acid molecule.

3. The immunogenic composition of claim 1 further comprising a live whole vaccine against a feline pathogen, or an inactivated whole vaccine against a feline pathogen, or recombinant vaccine against a feline pathogen, or a subunit vaccine against a feline pathogen.

4. A method for inducing an immunological response in a feline comprising: administering to said feline an immunogenic composition as claimed in any one of claims 1, 2, 3.

5. A method for inducing an immunological response in a feline comprising: administering to said feline an immunogenic composition selected from the group consisting of a live whole vaccine, an inactivated whole vaccine, a subunit vaccine, and a recombinant vaccine; and thereafter, administering to said feline an immunogenic composition as claimed in any one of claims 1, 2, or 3.

6. A method for inducing an immunological response in a feline comprising: administering to said feline an immunogenic composition selected from the group consisting of a live whole vaccine, an inactivated whole vaccine, a subunit vaccine, and a recombinant vaccine; and two to six weeks thereafter, admire stering to, said feline an immunogenic composition as claimed in any one of claims 1, 2, or 3.

7. A method for inducing an immunological response in a feline comprising: administering to said feline an immunogenic composition as claimed in any one of claims 1, 2, or 3 in combination with a live whole vaccine against a feline pathogen, or an inactivated whole vaccine against a feline pathogen, or recombinant vaccine against a feline pathogen, or a subunit vaccine against a feline pathogen.

8. A kit comprising (i) an immunogenic composition according to claim 1, and (ii) a feline vaccine selected from the group consisting of a live whole vaccine, an inactivated whole vaccine, a subunit vaccine, and recombinant vaccine.

9. A plasmid that contains and expresses in vivo in a feline host cell a nucleic acid molecule having a sequence encoding infectious peritonitis virus M protein. infectious peritonitis virus M protein.

10. A vaccine for inducing in a feline host an immunological response against infectious peritonitis virus comprising a plasmid that contains and expresses in vivo in a feline host cell a nucleic acid molecule having a sequence encoding infectious peritonitis virus M protein.

11. The vaccine of claim 10 wherein the plasmid further comprises a cytomeglovirus early (CMV-IE) promoter operatively linked to the nucleic acid molecule.

12. The vaccine of claim 10 further comprising a live whole vaccine against a feline pathogen, or an inactivated whole vaccine against a feline pathogen, or recombinant vaccine against a feline pathogen, or a subunit vaccine against a feline pathogen.

13. A method for vaccinating a feline comprising: administering to said feline a vaccine as claimed in any one of claims 10, 11, or 12.

14. A method for vaccinating a feline comprising: administering to said feline a vaccine selected from the group consisting of a live whole vaccine, an inactivated whole vaccine, a subunit vaccine, and a recombinant vaccine; and thereafter, administering to said feline a vaccine as claimed in any one of claims 10, 11, or 12.

15. A method vaccinating a feline comprising: administering to said feline a vaccine selected from the group consisting of a live whole vaccine, an inactivated whole vaccine, a subunit vaccine, and a recombinant vaccine; and two to six weeks thereafter, administering to said feline a vaccine composition as claimed in any one of claims 10, 11 or 12.

16. A method for vaccinating a feline comprising: administering to said feline a vaccine as claimed in any one of claims 10, 11, or 14 in combination with a live whole vaccine against a feline pathogen, or an inactivated whole vaccine against a feline pathogen, or recombinant vaccine against a feline pathogen, or a subunit vaccine against a feline pathogen.

* * * * *

UNITED STATES PATENT AND TRADEMARK OFFICE
CERTIFICATE OF CORRECTION

PATENT NO. : 6,348,196 B1
DATED : February 19, 2002
INVENTOR(S) : Jean-Christophe Audonnet et al.

It is certified that error appears in the above-identified patent and that said Letters Patent is hereby corrected as shown below:

Title page,
Item [75], Inventors, change "Lyons" to -- Lyon --.
Item [73], Assignee, change "Lyons" to -- Lyon --.

Column 26,
Line 27, after "method" insert -- for --.

Signed and Sealed this

Second Day of July, 2002

Attest:

JAMES E. ROGAN
*Attesting Officer*     *Director of the United States Patent and Trademark Office*